(12) United States Patent
Knappe et al.

(10) Patent No.: US 8,741,273 B2
(45) Date of Patent: Jun. 3, 2014

(54) AGENTS FOR FIBERS CONTAINING KERATIN, CONTAINING AT LEAST ONE SPECIAL CROSS-LINKED AMPHIPHILIC, ANIONIC POLYMER AND AT LEAST ONE FURTHER SPECIAL NON-CROSS-LINKED AMPHIPHILIC ANIONIC POLYMER

(75) Inventors: Thorsten Knappe, Schenefeld (DE); René Scheffler, Ellerau (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

(21) Appl. No.: 13/248,090

(22) Filed: Sep. 29, 2011

(65) Prior Publication Data
US 2012/0064023 A1 Mar. 15, 2012

Related U.S. Application Data

(63) Continuation of application No. PCT/EP2010/053699, filed on Mar. 22, 2010.

(30) Foreign Application Priority Data

Mar. 30, 2009 (DE) .......................... 10 2009 001 978

(51) Int. Cl.
*A61Q 5/06* (2006.01)
(52) U.S. Cl.
USPC .................. 424/70.11; 424/70.15; 424/70.16
(58) Field of Classification Search
None
See application file for complete search history.

(56) References Cited

U.S. PATENT DOCUMENTS

| 6,871,652 | B1 * | 3/2005 | Mueller et al. | 132/202 |
| 7,332,466 | B2 | 2/2008 | Schmid et al. | |
| 2006/0013785 | A1 * | 1/2006 | Lauscher et al. | 424/70.9 |
| 2006/0134049 | A1 * | 6/2006 | Keenan et al. | 424/70.15 |
| 2009/0041683 | A1 * | 2/2009 | Molenda et al. | 424/47 |
| 2009/0226390 | A1 * | 9/2009 | Birkel | 424/70.13 |

FOREIGN PATENT DOCUMENTS

| EP | 1997472 A1 | 12/2008 |
| WO | 2008098717 A2 | 8/2008 |

OTHER PUBLICATIONS

"Aculyn 88—more than just a thickener", Rohm and Haas Personal Care, Apr. 2005, pp. 1-2.
Collin, Reichl et al. "Aculyn TM 88 Rheology modifier", Research Disclosure, Kenneth Mason Publications, Ltd., vol. 494, No. 11, Jun. 2005.

* cited by examiner

*Primary Examiner* — Jyothsna Venkat
(74) *Attorney, Agent, or Firm* — Ingrassia Fisher & Lorenz, P.C.

(57) ABSTRACT

Agents for treating fibers containing keratin containing in a cosmetically acceptable carrier (a) at least one cross-linked, amphiphilic, anionic polymer, comprising at least one structural unit of formula (I) and at least one structural unit of formula (II); and (b) at least one non-cross-linked, amphiphilic, anionic polymer, comprising at least one structural unit of the formula (III) and at least one structural unit of the formula (IV), said agents being suitable for temporarily deforming hair and for conditioning hair, in particular in the form of a hair cream or a hair gel.

6 Claims, No Drawings

AGENTS FOR FIBERS CONTAINING KERATIN, CONTAINING AT LEAST ONE SPECIAL CROSS-LINKED AMPHIPHILIC, ANIONIC POLYMER AND AT LEAST ONE FURTHER SPECIAL NON-CROSS-LINKED AMPHIPHILIC ANIONIC POLYMER

CROSS REFERENCE TO RELATED APPLICATIONS

This is a continuation of International Patent Application No. PCT/EP2010/053699 filed 22 Mar. 2010, which claims priority to German Patent Application No. 10 2009 001 978.2 filed 30 Mar. 2009, both of which are incorporated herein by reference.

The present invention relates to agents for treating hair comprising a combination of at least one specific crosslinked amphiphilic, anionic polymer with at least one additional specific uncrosslinked amphiphilic, anionic polymer, use of these agents for the temporary shaping and/or for the care of keratin-containing fibers, and hair gels based on these agents.

Keratin-containing fibers in principle include all animal hair (e.g., wool, horsehair, angora hair, furs, feathers and products or fabrics produced from them). However, keratinic fibers preferably concern human hair.

Today, a suitable looking hairstyle is generally regarded as an essential part of a well groomed appearance. Based on actual fashion trends, time and again hairstyles are considered chic which, for many types of hair, can only be formed or sustained over a longer period of up to several days by use of certain consolidating materials. Thus, hair treatments which provide a permanent or temporary hairstyling play an important role. Temporary styling intended to provide a good hold, without compromising the healthy appearance of the hair, such as gloss, can be obtained for example by use of hairsprays, hair waxes, hair gels, hair foams, setting lotions, etc.

Suitable compositions for temporary hairstyling usually comprise synthetic polymers as the styling component. Preparations comprising a dissolved or dispersed polymer can be applied on the hair by propellants or by a pumping mechanism. Hair gels and hair waxes in particular, however, are not generally applied directly onto hair, but rather dispersed with a comb or by hand.

An important property of an agent for temporary styling of keratin fibers, also referred to as styling agents, consists in giving the treated fibers the strongest possible hold in the created shape. If the keratinic fibers are human hair, then one also speaks of a strong hairstyle hold or high degree of hold of the styling agent. Styling hold is determined by the type and quantity of synthetic polymer used, but there may also be an influence from other components of the styling agent.

In addition to a high degree of hold, styling agents must fulfill a whole series of additional requirements. These requirements can be broadly subdivided into properties on the hair, properties of the formulation in question (e.g., properties of the foam, gel or aerosol spray), and properties concerning the handling of the styling agent, wherein particular importance is attached to the hair properties. These include moisture resistance, low stickiness and a balanced conditioning effect. Furthermore, a styling agent should be universally applicable for as many types of hair as possible.

To do justice to the various requirements, various synthetic polymers have already been developed and are being used in styling agents. These polymers can be divided into cationic, anionic, non-ionic and amphoteric film-forming and/or setting polymers. Ideally these polymers form a polymer film when applied to hair, imparting a strong hold to the hairstyle while also being sufficiently flexible so not to break under stress. If the polymer film is too brittle, film plaques can develop (i.e., residues that are shed with movement of the hair and give the impression that the user of the respective styling agent has dandruff).

When the styling agent used is a gel, it has proved advantageous to prepare it as a clear, transparent gel. The consumer perceives clear gels as esthetically appealing, especially when gas bubbles are also incorporated in them. Unfortunately, it is often difficult to incorporate gas bubbles in conventional gel formulations. Even if gas bubbles were successfully incorporated into the conventional formulations, the gas bubbles would not be incorporated in a storage stable manner and would escape out of the gel.

To develop styling agents that in combination have all the desired properties still presents problems. This particularly applies to the combination of esthetic factors and strong and flexible hold. In order to impart a strong hold, the setting polymer has to adhere well to the keratin-containing fibers and form a sufficiently hard film. Nevertheless, the resulting polymer film should not lend the tactility of a board to the collective fibers, but rather impart a degree of flexibility to the fibers without losing the marked styling of the collective fibers (i.e., hair style).

Accordingly, the present invention provides an agent for temporary styling of keratinic fibers that has a very high degree of hold and does not form film plaques. Moreover, the agent should have an increased tolerance to salt and an improved soft feel (creaminess) without the addition of fats.

It has now been surprisingly found that this can be achieved by the inventive polymer combination discussed below.

Accordingly, a first subject matter of the present invention is agents for treating keratin-containing fibers, especially human hair, comprising in a cosmetically acceptable carrier—
(a) at least one crosslinked amphiphilic, anionic polymer, containing at least one structural unit of Formula (I) and at least one structural unit of Formula (II)

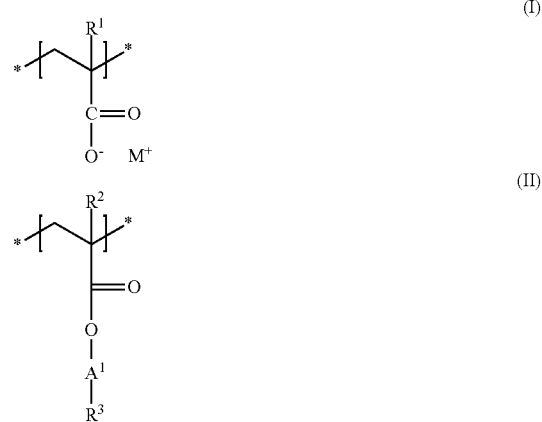

wherein
R$^1$ and R$^2$ are independently a hydrogen atom or a methyl group,
R$^3$ is a (C$_8$ to C$_{30}$) alkyl group,
M$^+$ is a physiologically acceptable cation, and
A$^1$ is *—(CH$_2$CH$_2$O)$_x$—* wherein x is a whole number from 5 to 35, *—(CH$_2$CHMeO)$_y$—* wherein y is a whole number from 5 to 35, or *—(CH$_2$CH$_2$O)$_x$—

(CH$_2$CHMeO)$_y$—* wherein the sum of x+y is a whole number from 5 to 35 and x and y are greater than zero; and (b) at least one uncrosslinked, amphiphilic, anionic polymer, containing at least one structural unit of Formula (III) and at least one structural unit of Formula (IV)

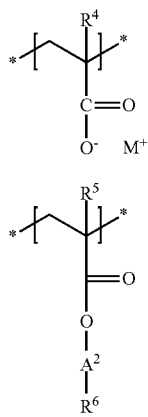

wherein
R$^4$ and R$^5$ are independently a hydrogen atom or a methyl group,
R$^6$ is a (C$_8$ to C$_{30}$) alkyl group,
M$^+$ is a physiologically acceptable cation, and
A$^2$ is *—(CH$_2$CH$_2$O)$_x$—* wherein x is a whole number from 5 to 35, *—(CH$_2$CHMeO)$_y$—* wherein y is a whole number from 5 to 35, or *—(CH$_2$CH$_2$O)$_x$—(CH$_2$CHMeO)$_y$—* wherein the sum x+y is a whole number from 5 to 35 and x and y are greater than zero.

Exemplary inventive (C$_1$ to C$_4$) alkyl groups are methyl, ethyl, propyl, isopropyl, butyl, sec-butyl, isobutyl, tert-butyl.

Exemplary inventive (C$_8$ to C$_{30}$) alkyl groups are octyl (capryl), decyl (caprinyl), dodecyl (lauryl), tetradecyl (myristyl), hexadecyl (cetyl), octadecyl (stearyl), eicosyl (arachyl), docosyl (behenyl).

In the above Formulae and all Formulae below, the symbol * signifies a chemical bond that is a free valence of the corresponding structural fragment.

Metal cations of the physiologically acceptable metals of Groups Ia, Ib, IIa, IIb, Mb, VIa or VIII of the Periodic Table, ammonium ions, as well as cationic organic compounds containing a quaternized nitrogen atom, are particularly suitable as the physiologically acceptable cations M$^+$ for compensating the negative charge of the amphiphilic, anionic polymers. Cationic organic compounds containing a quaternized nitrogen atom are formed for example by protonating primary, secondary or tertiary organic amines with an acid, or by the permanent quaternization of the cited organic amines. Examples of these cationic organic ammonium compounds are 2-ammonioethanol and 2-trimethylammonioethanol.

In the context of the invention, "crosslinked" or "crosslinking" is understood to mean the linkage of polymer chains with one another through covalent chemical bonding with the formation of a network. This covalent linkage of the polymer chains may result from direct covalent bonds or be imparted by a molecular fragment that connects the polymer chains together. The molecular fragment bonds to each of the polymer chains connected by the molecular fragment by means of a covalent chemical bond. In the context of the invention, "uncrosslinked" is understood to mean that no previously defined "crosslinking" exists.

In general, one skilled in the art understands "amphiphilic" to mean that one and the same molecule contains hydrophilic structural elements (e.g., those of Formulas (I) or (III)) and lipophilic structural elements (e.g., those of Formulas (II) or (IV)).

In Formula (II), A$^1$ preferably is *—(CH$_2$CH$_2$O)$_x$—*, wherein x is a whole number from 5 to 35, especially a whole number from 10 to 24.

In Formula (II), R$^2$ preferably is a methyl group.

Crosslinking of the crosslinked, amphiphilic, anionic polymers (a) can preferably be effected by use of at least one crosslinking monomer. Here it is again preferred to choose the crosslinking monomer from at least one of polyunsaturated aromatic monomers (such as divinylbenzene, divinylnaphthalene, trivinylbenzene), polyunsaturated alicyclic monomers (such as 1,2,4-trivinylcyclohexane), di-functional esters of phthalic acid (such as diallyl phthalate), polyunsaturated aliphatic monomers (such as dienes, trienes, tetraenes such as isoprene, 1,3-butadiene, 1,5-hexadiene, 1,5,9-decatriene, 1,9-decadiene, 1,5-heptadiene), polyalkenyl ethers (such as triallyl pentaerythritol, diallyl pentaerythritol, diallyl sucrose, octaallyl sucrose, trimethylolpropane diallyl ether), polyunsaturated esters of polyalcohols or polyacids (such as 1,6-hexane diol di(meth)acrylate, tetramethylene tri(meth)acrylate, allyl acrylate, diallyl itaconate, diallyl fumarate, diallyl maleate, trimethylolpropane tri(meth)acrylate, trimethylolpropane di(meth)acrylate, polyethylene glycol di(meth)acrylate), alkylene bisacrylamides (such as methylene bisacrylamide, propylene bisacrylamide) hydroxy and carboxy derivatives of methylene bisacrylamide (such as N,N'-bismethylolmethylene bisacrylamide), polyethylene glycol di(meth)acrylates (such as ethylene glycol di(meth)acrylate, diethylene glycol di(meth)acrylate, triethylene glycol di(meth)acrylate), polyunsaturated silanes (such as for example dimethyldivinylsilane, methyltrivinylsilane, allyldimethylvinylsilane, diallyldimethylsilane, tetravinylsilane), N-methylolacrylamide; N-alkoxy(meth)acrylamides, wherein the alkoxy group is a (C$_1$ to C$_{18}$) alkoxy group, unsaturated hydrolyzable silanes (such as triethoxy vinylsilane, trisisopropoxy vinylsilane, 3-triethoxy silylpropylmethacrylate), hydrolyzable silanes (such as for example ethyltriethoxysilane, ethyltrimethoxysilan), epoxy-substituierte hydrolysierbare silane (such as 2-(3,4-epoxycyclohexyl)ethyltriethoxysilane, 3-glycidoxypropyltrimethyoxysilane) polyisocyanates (such as 1,4-diisocyanatobutane, 1,6-diisocyanatohexane, 1,4-phenylenediisocyanate, 4,4'-oxybis (phenylisocyanate), unsaturated epoxides (such as glycidyl methacrylate, allyl glycidyl ether), polyepoxides (such as diglycidyl ether, 1,2,5,6-diepoxyhexane, ethylene glycol diglycidyl ether), ethoxylated polyols (such as diols, triols and diphenols, each ethoxylated with 2 to 100 mol ethylene oxide per mol hydroxyl groups and terminated with a polymerizable unsaturated group, such as vinyl ether, allyl ether, acrylate ester, methacrylate ester; for example including ethoxylated bisphenol A di(meth)acrylate, ethoxylated bisphenol F di(meth)acrylate, ethoxylated trimethylolpropane tri(meth) acrylate, acrylate and methacrylate esters of polyols with at least two acrylate ester or methacrylate ester functionalities (such as trimethylolpropane triacrylate (TMPTA), trimethylolpropane ethoxylated (15) triacrylate (TMPEO15TA), trimethylolpropane dimethacrylate, triethylene glycol dimethacrylate (TEGDMA), bisphenol A dimethacrylate ethoxylated with 30 mol ethylene oxide (EOBDMA)).

Agents according to the invention preferably comprise crosslinked, amphiphilic, anionic polymers (a) in an amount of 0.1 wt. % to 5.0 wt. %, more preferably 0.2 wt. % to 2.0 wt. %, quite particularly preferably 0.2 wt. % to 1.5 wt. %, based on total weight of the agent.

Particularly preferred crosslinked amphiphilic anionic polymers (a) according to the invention additionally comprise at least one structural unit of Formula (V)—

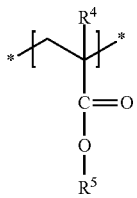

(V)

wherein
$R^4$ is a hydrogen atom or a methyl group,
$R^5$ is a ($C_2$ to $C_4$) alkyl group, especially ethyl.

It is inventively preferred to select at least one polymer containing at least one structural unit of Formula (I) and at least one structural unit of Formula (II) as the crosslinked amphiphilic, anionic polymer (a)—

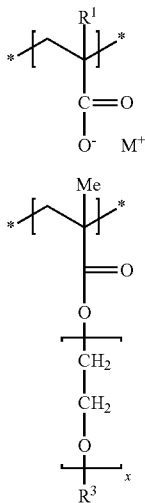

(I)

(II-a)

wherein
$R^1$ is a hydrogen atom or a methyl group,
$R^3$ is a ($C_8$ to $C_{30}$) alkyl group,
$M^+$ is a physiologically acceptable cation, and
x is a whole number from 5 to 35, especially a whole number from 10 to 24.

Moreover, it is particularly preferred to select the crosslinked, amphiphilic, anionic polymer (a) from at least one polymer, containing at least one structural unit of Formula (I) and at least one structural unit of Formula (II-a) and at least one structural unit of Formula (V)—

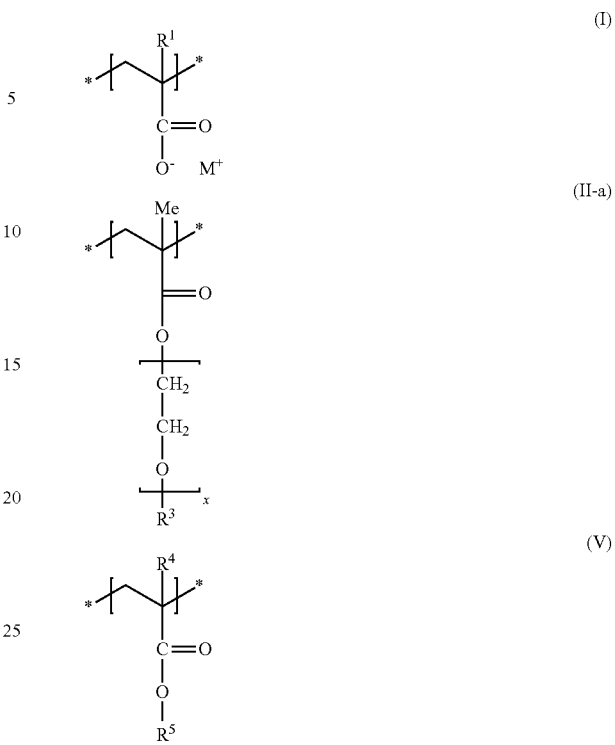

(I)

(II-a)

(V)

wherein
$R^1$ and $R^4$ are independently a hydrogen atom or a methyl group,
$R^3$ is a ($C_8$ to $C_{30}$) alkyl group,
$R^5$ is a ($C_2$ to $C_4$) alkyl group, especially ethyl,
$M^+$ is a physiologically acceptable cation, and
x is a whole number from 5 to 35, especially a whole number from 10 to 24.

A quite particularly preferred polymer (a) is a crosslinked, amphiphilic, anionic polymer having the INCI name Acrylates/Steareth-20 Methacrylate Crosspolymer. It possesses 20 ethylene oxide units (x according to Formula (II-a)=20) and is etherified with stearyl alcohol ($R^3$ according to Formula (II-a)=stearyl). Polymers of this type are marketed for example under the trade name Aculyn® 88 by Rohm & Haas in the form of a 28 to 30 wt. % conc. dispersion in water.

Further, the agent according to the invention comprises, in addition to the previously defined crosslinked amphiphilic, anionic polymers, at least one previously defined uncrosslinked, amphiphilic, anionic polymer (b).

In the context of the invention, preferred agents comprise uncrosslinked, amphiphilic, anionic polymers (b) in an amount of 0.1 wt. % to 5.0 wt. %, preferably 0.2 wt. % to 5.0 wt. %, more preferably 0.1 wt. % to 2.0 wt. %, based on total weight of the agent.

Crosslinked, amphiphilic, anionic polymers (a) and uncrosslinked, amphiphilic, anionic polymers (b) are inventively preferably employed in a weight ratio [polymer (a) to polymer (b)] of 1 to 5 to 5 to 1, particularly 1 to 2 to 5 to 1, quite particularly preferably 1 to 1.5 to 2 to 1.

In Formula (IV) $A^2$ preferably is *—$(CH_2CH_2O)_x$—*, wherein x is a whole number from 5 to 35, especially a whole number from 15 to 30.

$R^5$ of Formula (IV) preferably is a hydrogen atom.

Particularly preferred uncrosslinked amphiphilic anionic polymers (b) according to the invention additionally comprise at least one structural unit of Formula (V)—

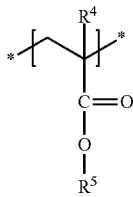
(V)

wherein $R^4$ is a hydrogen atom or a methyl group, and $R^5$ is a ($C_2$ to $C_4$) alkyl group, especially ethyl.

Preferably, the uncrosslinked, amphiphilic, anionic polymers (b) contain at least one structural unit of Formula (I) and at least one structural unit of Formula (IV-a)—

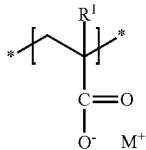
(I)

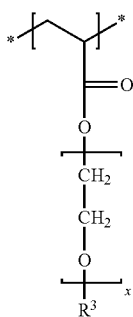
(IV-a)

wherein $R^1$ is a hydrogen atom or a methyl group, $R^3$ is a ($C_8$ to $C_{30}$) alkyl group, $M^+$ is a physiologically acceptable cation, and x is a whole number from 5 to 35, especially a whole number from 15 to 30.

Moreover, it is particularly preferred to select the uncrosslinked, amphiphilic, anionic polymers (b) from at least one polymer having at least one structural unit of Formula (I), at least one structural unit of Formula (IV-a), and at least one structural unit of Formula (V)—

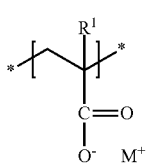
(I)

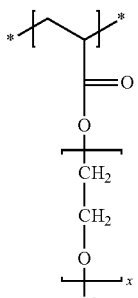
(IV-a)

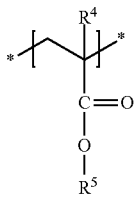
(V)

wherein $R^1$ and $R^4$ are independently a hydrogen atom or a methyl group, $R^3$ is a ($C_8$ to $C_{30}$) alkyl group, $R^5$ is a ($C_2$ to $C_4$) alkyl group, especially ethyl, $M^+$ is a physiologically acceptable cation, and x is a whole number from 5 to 35, especially a whole number from 15 to 30.

A quite particularly preferred uncrosslinked, amphiphilic, anionic polymer (b) possesses 25 ethylene oxide units (x in Formula (IV-a)=25), is etherified with palm fatty alcohol ($R^3$ in Formula (IV-a)=alkyl chain distribution of the palm oil fatty acids) and is named according to the INCI nomenclature as Acrylates/Palmeth-25 Acrylate Copolymer. Accordingly, the agents according to the invention quite particularly preferably comprise at least one uncrosslinked, amphiphilic, anionic polymer that falls under the INCI name Acrylates/Palmeth-20 Acrylate Copolymer. A polymer of this type is available for example from the 3 V Sigma company under the trade name Synthalen® W 2000 as a 30 to 32 wt. % conc. emulsion in water.

The following embodiments (A) to (I) illustrate quite particularly preferred embodiments of the agent according to the invention:

(A): An agent for treating keratin-containing fibers, especially human hair, comprising in a cosmetically acceptable carrier—

(a) at least one crosslinked, amphiphilic, anionic polymer, containing at least one structural unit of Formula (I) and at least one structural unit of Formula (II-a)—

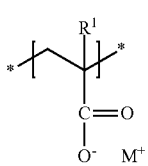
(I)

-continued

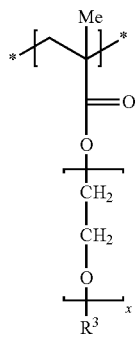
(II-a)

wherein
R$^1$ is a hydrogen atom or a methyl group,
R$^3$ is a (C$_8$ to C$_{30}$) alkyl group,
M$^+$ is a physiologically acceptable cation, and
x is a whole number from 5 to 35, especially a whole number from 10 to 24; and (b) at least one uncrosslinked amphiphilic, anionic polymer, containing at least one structural unit of Formula (III) and at least one structural unit of Formula (IV)

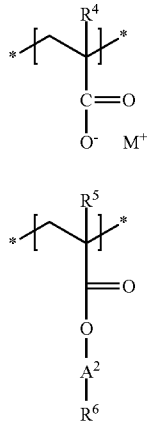
(III)

(IV)

wherein
R$^4$ and R$^5$ are independently a hydrogen atom or a methyl group,
R$^6$ is a (C$_8$ to C$_{30}$) alkyl group,
M$^+$ is a physiologically acceptable cation, and
A$^2$ is *—(CH$_2$CH$_2$O)$_x$—* wherein x is a whole number from 5 to 35, *—(CH$_2$CHMeO)$_y$—* wherein y is a whole number from 5 to 35, or *—(CH$_2$CH$_2$O)$_x$—(CH$_2$CHMeO)$_y$—* wherein the sum of x+y is a whole number from 5 to 35 and x and y are greater than zero.

(B): An agent for treating keratin-containing fibers, especially human hair, comprising in a cosmetically acceptable carrier—

(a) at least one crosslinked, amphiphilic, anionic polymer, containing at least one structural unit of Formula (I) and at least one structural unit of Formula (II)—

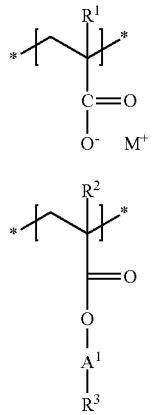
(I)

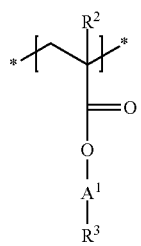
(II)

wherein
R$^1$ and R$^2$ are independently a hydrogen atom or a methyl group,
R$^3$ is a (C$_8$ to C$_{30}$) alkyl group,
M$^+$ is a physiologically acceptable cation, and
A$^1$ is *—(CH$_2$CH$_2$O)$_x$—* wherein x is a whole number from 5 to 35, *—(CH$_2$CHMeO)$_y$—* wherein y is a whole number from 5 to 35, or *—(CH$_2$CH$_2$O)$_x$—(CH$_2$CHMeO)$_y$—* wherein the sum x+y is a whole number from 5 to 35 and x and y are greater than zero; and (b) at least one uncrosslinked amphiphilic, anionic polymer, containing at least one structural unit of Formula (III) and at least one structural unit of Formula (IV-a)

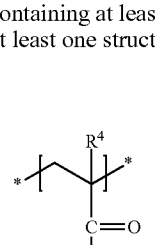
(III)

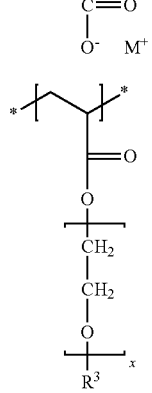
(IV-a)

wherein
R$^4$ is a hydrogen atom or a methyl group,
R$^3$ is a (C$_8$ to C$_{30}$) alkyl group,
M$^+$ is a physiologically acceptable cation, and
x is a whole number from 5 to 35, especially a whole number from 15 to 30.

(C): An agent for treating keratin-containing fibers, especially human hair, comprising in a cosmetically acceptable carrier—

(a) at least one crosslinked, amphiphilic, anionic polymer, containing at least one structural unit of Formula (I) and at least one structural unit of Formula (II-a)—

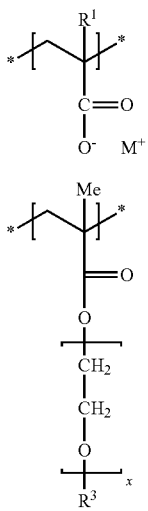

(I)

(II-a)

wherein
R$^1$ is a hydrogen atom or a methyl group,
R$^3$ is a (C$_8$ to C$_{30}$) alkyl group,
M$^+$ is a physiologically acceptable cation, and
x is a whole number from 5 to 35, especially a whole number from 10 to 24; and
(b) at least one uncrosslinked amphiphilic, anionic polymer, containing at least one structural unit of Formula (III) and at least one structural unit of Formula (IV-a)

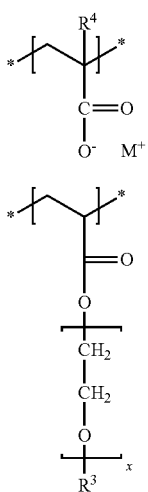

(III)

(IV-a)

wherein
R$^4$ is a hydrogen atom or a methyl group,
R$^3$ is a (C$_8$ to C$_{30}$) alkyl group,
M$^+$ is a physiologically acceptable cation, and
x is a whole number from 5 to 35, especially a whole number from 15 to 30.

(D): An agent for treating keratin-containing fibers, especially human hair, comprising in a cosmetically acceptable carrier—
(a) 0.1 wt. % to 5.0 wt. %, preferably 0.2 wt. % to 2 wt. %, more preferably 0.2 wt. % to 1.5 wt. %, based on total weight of the agent, of at least one crosslinked, amphiphilic, anionic polymer containing at least one structural unit of Formula (I) and at least one structural unit of Formula (II-a)—

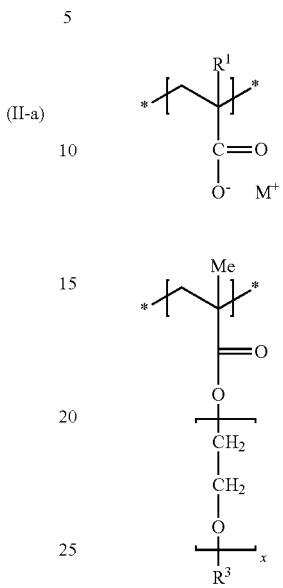

(I)

(II-a)

wherein
R$^1$ is a hydrogen atom or a methyl group,
R$^3$ is a (C$_8$ to C$_{30}$) alkyl group,
M$^+$ is a physiologically acceptable cation, and
x is a whole number from 5 to 35, especially a whole number from 10 to 24; and
(b) 0.1 wt. % to 5.0 wt. %, preferably 0.2 wt. % to 5.0 wt. %, more preferably 0.1 wt. % to 2.0 wt. %, based on total weight of the agent, of at least one uncrosslinked amphiphilic, anionic polymer containing at least one structural unit of Formula (III) and at least one structural unit of Formula (IV)

(III)

(IV)

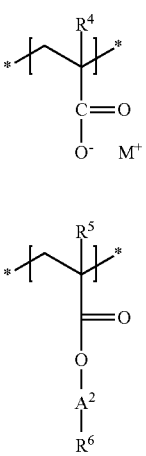

wherein
R$^4$ and R$^5$ are independently a hydrogen atom or a methyl group,
R$^6$ is a (C$_8$ to C$_{30}$) alkyl group,
M$^+$ is a physiologically acceptable cation, and $A^2$ is *—$(CH_2CH_2O)_x$—* wherein x is a whole number from 5 to 35, *—$(CH_2CHMeO)_y$—* wherein y is a whole number from 5 to 35, or *—$(CH_2CH_2O)_x$—$(CH_2CHMeO)_y$—* wherein the sum of x+y is a whole number from 5 to 35 and x and y are greater than zero.

(E): An agent for treating keratin-containing fibers, especially human hair, comprising in a cosmetically acceptable carrier—

(a) 0.1 wt. % to 5.0 wt. %, preferably 0.2 wt. % to 2 wt. %, more preferably 0.2 wt. % to 1.5 wt. %, based on total weight of the agent, of at least one crosslinked, amphiphilic, anionic polymer containing at least one structural unit of Formula (I) and at least one structural unit of Formula (II)—

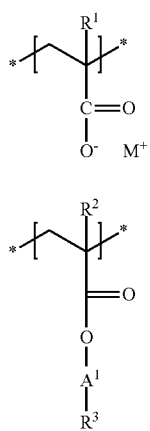

(I)

(II)

wherein $R^1$ and $R^2$ are independently a hydrogen atom or a methyl group, $R^3$ is a ($C_8$ to $C_{30}$) alkyl group, $M^+$ is a physiologically acceptable cation, and $A^1$ is *—$(CH_2CH_2O)_x$—* wherein x is a whole number from 5 to 35, *—$(CH_2CHMeO)_y$—* wherein y is a whole number from 5 to 35, or *—$(CH_2CH_2O)_x$—$(CH_2CHMeO)_y$—* wherein the sum x+y is a whole number from 5 to 35 and x and y are greater than zero; and (b) 0.1 wt. % to 5.0 wt. %, preferably 0.2 wt. % to 5.0 wt. %, more preferably 0.1 wt. % to 2.0 wt. %, based on total weight of the agent, of at least one uncrosslinked amphiphilic, anionic polymer containing at least one structural unit of Formula (III) and at least one structural unit of Formula (IV-a)

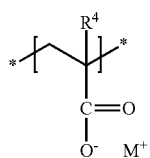

(III)

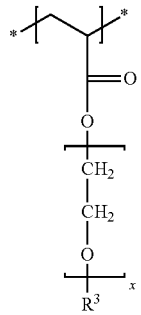

(IV-a)

wherein $R^4$ is a hydrogen atom or a methyl group, $R^3$ is a ($C_8$ to $C_{30}$) alkyl group, $M^+$ is a physiologically acceptable cation, and x is a whole number from 5 to 35, especially a whole number from 15 to 30.

(F): An agent for treating keratin-containing fibers, especially human hair, comprising in a cosmetically acceptable carrier—

(a) 0.1 wt. % to 5.0 wt. %, preferably 0.2 wt. % to 2 wt. %, more preferably 0.2 wt. % to 1.5 wt. %, based on total weight of the agent, of at least one crosslinked, amphiphilic, anionic polymer containing at least one structural unit of Formula (I) and at least one structural unit of Formula (II-a)—

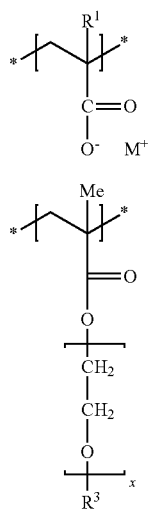

(I)

(II-a)

wherein $R^1$ is a hydrogen atom or a methyl group, $R^3$ is a ($C_8$ to $C_{30}$) alkyl group, $M^+$ is a physiologically acceptable cation, and x is a whole number from 5 to 35, especially a whole number from 10 to 24; and (b) 0.1 wt. % to 5.0 wt. %, preferably 0.2 wt. % to 5.0 wt. %, more preferably 0.1 wt. % to 2.0 wt. %, based on total weight of the agent, of at least one uncrosslinked amphiphilic, anionic polymer containing at least one structural unit of Formula (III) and at least one structural unit of Formula (IV-a)

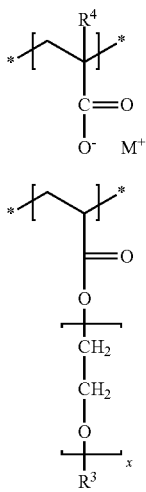

(III)

(IV-a)

wherein
R⁴ is a hydrogen atom or a methyl group,
R³ is a ($C_s$ to $C_{30}$) alkyl group,
M⁺ is a physiologically acceptable cation, and
x is a whole number from 5 to 35, especially a whole number from 15 to 30.

(G): An agent for treating keratin-containing fibers, especially human hair, comprising in a cosmetically acceptable carrier—
(a) 0.1 wt. % to 5.0 wt. %, preferably 0.2 wt. % to 2 wt. %, more preferably 0.2 wt. % to 1.5 wt. %, based on total weight of the agent, of at least one crosslinked, amphiphilic, anionic polymer containing at least one structural unit of Formula (I) and at least one structural unit of Formula (II-a)—

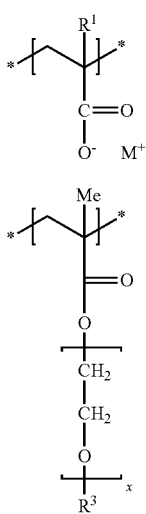

(I)

(II-a)

wherein
R¹ is a hydrogen atom or a methyl group,
R³ is a ($C_8$ to $C_{30}$) alkyl group,
M⁺ is a physiologically acceptable cation, and
x is a whole number from 5 to 35, especially a whole number from 10 to 24; and (b) 0.1 wt. % to 5.0 wt. %, preferably 0.2 wt. % to 5.0 wt. %, more preferably 0.1 wt. % to 2.0 wt. %, based on total weight of the agent, of at least one uncrosslinked amphiphilic, anionic polymer containing at least one structural unit of Formula (III) and at least one structural unit of Formula (IV)

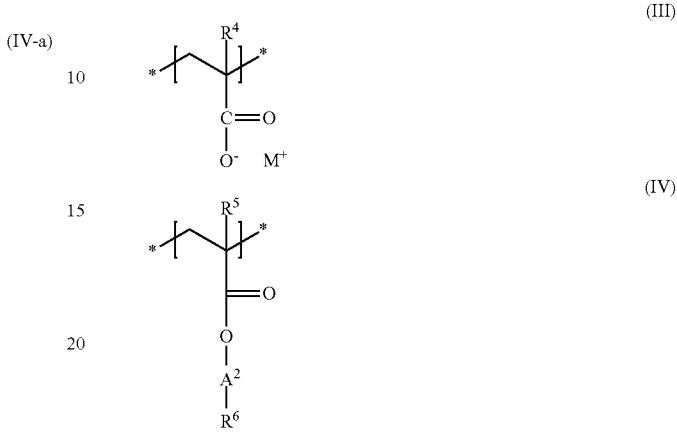

wherein
R⁴ and R⁵ are independently a hydrogen atom or a methyl group,
R⁶ is a ($C_8$ to $C_{30}$) alkyl group,
M⁺ is a physiologically acceptable cation, and
A² is *—$(CH_2CH_2O)_x$—* wherein x is a whole number from 5 to 35, *—$(CH_2CHMeO)_y$—* wherein y is a whole number from 5 to 35, or *—$(CH_2CH_2O)_x$—$(CH_2CHMeO)_y$—* wherein the sum of x+y is a whole number from 5 to 35 and x and y are greater than zero,
in a weight ratio [polymer (a) to polymer (b)] of 1 to 5 to 5 to 1, preferably 1 to 2 to 5 to 1, more preferably 1 to 1.5 to 2 to 1.

(H): An agent for treating keratin-containing fibers, especially human hair, comprising in a cosmetically acceptable carrier—
(a) 0.1 wt. % to 5.0 wt. %, preferably 0.2 wt. % to 2 wt. %, more preferably 0.2 wt. % to 1.5 wt. %, based on total weight of the agent, of at least one crosslinked, amphiphilic, anionic polymer containing at least one structural unit of Formula (I) and at least one structural unit of Formula (II)—

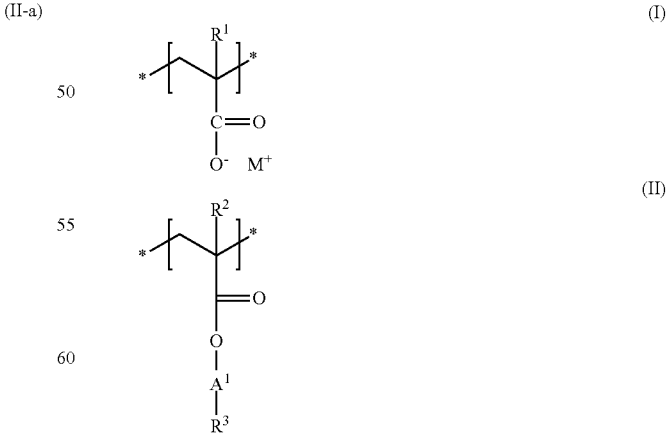

(I)

(II)

wherein
R¹ and R² are independently a hydrogen atom or a methyl group, $R^3$ is a ($C_8$ to $C_{30}$) alkyl group, $M^+$ is a physiologically acceptable cation, and $A^1$ is *—$(CH_2CH_2O)_x$—* wherein x is a whole number from 5 to 35, *—$(CH_2CHMeO)_y$—* wherein y is a whole number from 5 to 35, or *—$(CH_2CH_2O)_x$—$(CH_2CHMeO)_y$—* wherein the sum x+y is a whole number from 5 to 35 and x and y are greater than zero; and (b) 0.1 wt. % to 5.0 wt. %, preferably 0.2 wt. % to 5.0 wt. %, more preferably 0.1 wt. % to 2.0 wt. %, based on total weight of the agent, of at least one uncrosslinked amphiphilic, anionic polymer containing at least one structural unit of Formula (III) and at least one structural unit of Formula (IV-a)

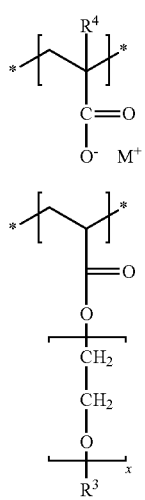

(III)

(IV-a)

wherein $R^4$ is a hydrogen atom or a methyl group, $R^3$ is a ($C_8$ to $C_{30}$) alkyl group, $M^+$ is a physiologically acceptable cation, and x is a whole number from 5 to 35, especially a whole number from 15 to 30, in a weight ratio [polymer (a) to polymer (b)] of 1 to 5 to 5 to 1, preferably 1 to 2 to 5 to 1, more preferably 1 to 1.5 to 2 to 1.

(I): An agent for treating keratin-containing fibers, especially human hair, comprising in a cosmetically acceptable carrier—

(a) 0.1 wt. % to 5.0 wt. %, preferably 0.2 wt. % to 2 wt. %, more preferably 0.2 wt. % to 1.5 wt. %, based on total weight of the agent, of at least one crosslinked, amphiphilic, anionic polymer containing at least one structural unit of Formula (I) and at least one structural unit of Formula (II-a)—

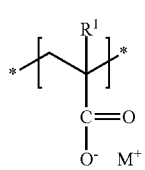

(I)

-continued

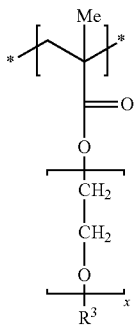

(II-a)

wherein $R^1$ is a hydrogen atom or a methyl group, $R^3$ is a ($C_8$ to $C_{30}$) alkyl group, $M^+$ is a physiologically acceptable cation, and x is a whole number from 5 to 35, especially a whole number from 10 to 24; and (b) 0.1 wt. % to 5.0 wt. %, preferably 0.2 wt. % to 5.0 wt. %, more preferably 0.1 wt. % to 2.0 wt. %, based on total weight of the agent, of at least one uncrosslinked amphiphilic, anionic polymer containing at least one structural unit of Formula (III) and at least one structural unit of Formula (IV-a)

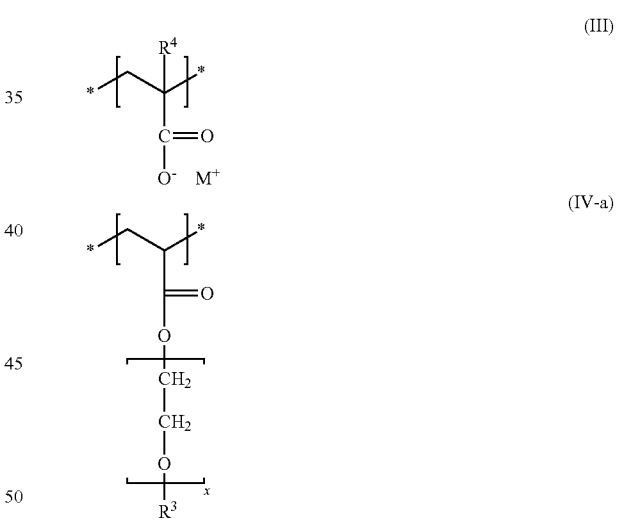

(III)

(IV-a)

wherein $R^4$ is a hydrogen atom or a methyl group, $R^3$ is a ($C_8$ to $C_{30}$) alkyl group, $M^+$ is a physiologically acceptable cation, and x is a whole number from 5 to 35, especially a whole number from 15 to 30, in a weight ratio [polymer (a) to polymer (b)] of 1 to 5 to 5 to 1, preferably 1 to 2 to 5 to 1, more preferably 1 to 1.5 to 2 to 1.

Here again it is preferred when embodiments (A) to (I) contain as polymer (a) at least one crosslinked amphiphilic anionic polymer (a) that additionally comprises at least one structural unit of Formula (V)—

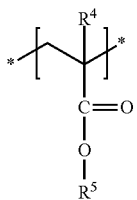

wherein
$R^4$ is a hydrogen atom or a methyl group, and
$R^5$ is a ($C_2$ to $C_4$) alkyl group, especially ethyl.

Furthermore it is again preferred when embodiments (A) to (I) contain as polymer (b) at least one uncrosslinked amphiphilic anionic polymer (b) that additionally comprises at least one structural unit of Formula (V)—

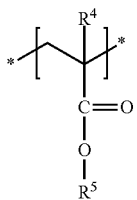

wherein
$R^4$ is a hydrogen atom or a methyl group, and
$R^5$ is a ($C_2$ to $C_4$) alkyl group, especially ethyl.

In a preferred embodiment, the agent according to the invention further comprises, in addition to the crosslinked, amphiphilic, anionic polymer (a) and the uncrosslinked amphiphilic, anionic polymer (b), at least one film-forming and/or setting polymer (c). The last polymer differs from the cited polymers (a) and (b).

The preferred properties of the film-forming polymers include film formation. Film-forming polymers refer to those polymers that on drying leave a continuous film on the skin, hair or nails. These types of film-former can be used in the widest variety of cosmetic products, such as make up masks, make up, hair sets, hair sprays, hair gels, hair waxes, hair conditioners, shampoos or nail varnishes. Those polymers are particularly preferred which are sufficiently soluble in alcohol or water/alcohol mixtures, such that they are present in completely dissolved form in the agents. Film-forming polymers can be of synthetic or natural origin.

According to the invention, film-forming polymers further refer to those polymers that, when used in concentrations of 0.1 to 20 wt. % in aqueous, alcoholic or aqueous alcoholic solution, are able to separate out a transparent polymer film on the hair.

Setting polymers contribute to the hold and/or creation of hair volume and hair body of the whole hairstyle. These polymers are also film-forming polymers and therefore in general are typical substances for styling hair treatment agents such as hair sets, hair foams, hair waxes, hair sprays. Film formation can be in completely selected areas and bond only some fibers together.

The curl-retention test is frequently used as a test method for setting action.

As polymers are often multifunctional (i.e., they show a plurality of desired end-use effects), a large number of polymers are to be found in many of the groups subdivided according to the mode of action, therefore also in the CTFA Handbook.

Agents according to the invention preferably comprise at least one film-forming and/or setting polymer chosen from at least one of non-ionic polymers, cationic polymers, amphoteric polymers, zwitterionic polymers and anionic polymers, preferably from non-ionic, cationic and amphoteric polymers.

Agents according to the invention preferably comprise film-forming and/or setting polymers in an amount of 0.01 wt. % to 10.0 wt. %, more preferably 0.5 wt. % to 8.0 wt. %, and particularly preferably 0.5 wt. % to 5.0 wt. %, based on total weight of the agent. These quantitative data also apply for all subsequent preferred types of film-forming and/or setting polymers that can be used in the inventive agents. Should subsequently different preferred quantities be specified, then the latter are to be again taken as the preferred quantities.

Those agents are particularly preferably suitable that comprise, besides the previously defined polymers (a) and (b), at least one film-forming and/or setting polymer chosen from at least one polymer of— non-ionic polymers based on ethylenically unsaturated monomers, especially
  homopolymers of N-vinyl pyrrolidone,
  non-ionic copolymers of N-vinyl pyrrolidone,
  homopolymers and non-ionic copolymers of N-vinyl caprolactam,
  copolymers of (meth)acrylamide, and
  polyvinyl alcohol, polyvinyl acetate;
chitosan and derivatives of chitosan;
cationic cellulose derivatives;
cationic copolymers of 3-($C_1$ to $C_6$) alkyl-1-vinyl-imidazolinium; and
homopolymers and copolymers comprising the structural unit of the Formula (M-1)

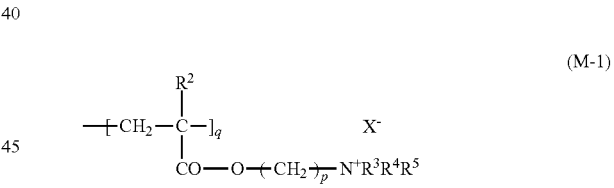

wherein $R^2$ is —H or —$CH_3$; $R^3$, $R^4$ and $R^5$ are independently chosen from ($C_t$ to $C_4$) alkyl, ($C_1$ to $C_4$) alkenyl or ($C_2$ to $C_4$) hydroxyalkyl groups; p is 1, 2, 3 or 4; q is a natural number; and $X^-$ is a physiologically acceptable organic or inorganic anion.

Preferred non-ionic polymers based on ethylenically unsaturated monomers, which are suitable as additional film-forming and/or setting polymers, are those non-ionic polymers that comprise at least one of the following structural units—

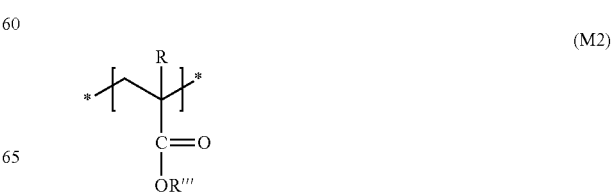

-continued

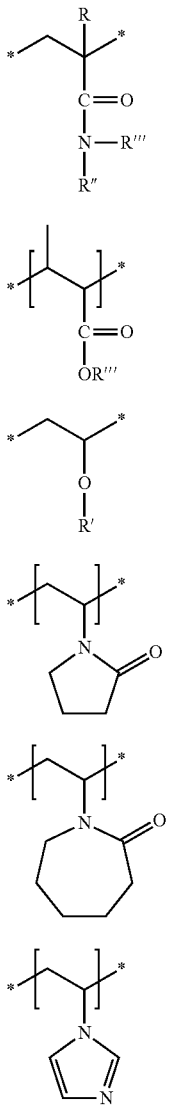

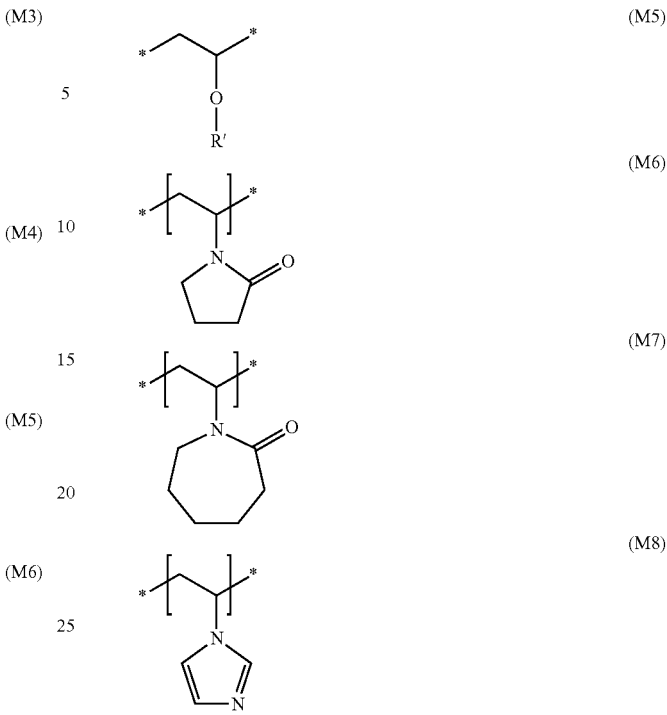

wherein
R is hydrogen or a methyl group,
R' is hydrogen or a ($C_1$ to $C_4$) acyl group,
R" and R"" are independently a ($C_1$ to $C_7$) alkyl group or hydrogen, and
R'" is a linear or branched ($C_1$ to $C_4$) alkyl group or a ($C_2$ to $C_4$) hydroxyalkyl group.

Suitable, non-ionic film-forming and/or non-ionic hair setting polymers include homopolymers or copolymers based on at least one of the following monomers: vinyl pyrrolidone, vinyl caprolactam, vinyl esters such as vinyl acetate, vinyl alcohol, acrylamide, methacrylamide, alkyl and dialkyl acrylamide, alkyl and dialkyl methacrylamide, alkyl acrylate, alkyl methacrylate, wherein each of the alkyl groups of these monomers are chosen from ($C_1$ to $C_3$) alkyl groups.

Particularly suitable non-ionic polymers based on ethylenically unsaturated monomers for agents according to the invention comprise at least one of the following structural units— wherein
R' is hydrogen or a ($C_1$— to $C_{30}$) acyl group, particularly hydrogen or an acetyl group.

Homopolymers of vinyl caprolactam or of vinyl pyrrolidone (such as Luviskol® K 90 or Luviskol® K 85 from BASF SE), copolymers of vinyl pyrrolidone and vinyl acetate (such as are marketed under the trade names Luviskol® VA 37, Luviskol® VA 55, Luviskol® VA 64 and Luviskol® VA 73 by BASF SE), terpolymers of vinyl pyrrolidone, vinyl acetate and vinyl propionate, polyacrylamides (such as Akypomine®P 191 from CHEM-Y), polyvinyl alcohols (marketed, for example, under the trade names Elvanol® by Du Pont or Vinol® 523/540 by Air Products), terpolymers of vinyl pyrrolidone, methacrylamide and vinyl imidazole (such as Luviset® Clear from BASF SE) are particularly suitable.

Besides non-ionic polymers based on ethylenically unsaturated monomers, non-ionic cellulose derivatives are also suitable film-forming and/or setting polymers for the preferred achievement of the technical teaching; they are preferably chosen from methyl cellulose, especially from cellulose ethers such as hydroxypropyl cellulose (e.g., hydroxypropyl cellulose with a molecular weight of 30 000 to 50 000 g/mol and marketed, for example, under the trade name Nisso SI® by Lehmann & Voss, Hamburg), hydroxyethyl celluloses, such as those marketed under the trade names Culminal and Benecel® (AQUALON) and Natrosol® types (Hercules).

Cationic polymers refer to polymers that, in their main chain and/or side chain, possess groups that can be "temporarily" or "permanently" cationic. "Permanently cationic" according to the invention refers to those polymers that exhibit a cationic group, independently of the pH of the medium. These are generally polymers having a quaternary nitrogen atom in the form of an ammonium group, for example. Preferred cationic groups are quaternary ammonium groups. In particular, those polymers in which the quaternary ammonium groups are bonded through a $C_{1-4}$ hydrocarbon group to a polymer backbone formed from acrylic acid, methacrylic acid or their derivatives have proved to be particularly suitable.

Homopolymers of the general formula (M1)—

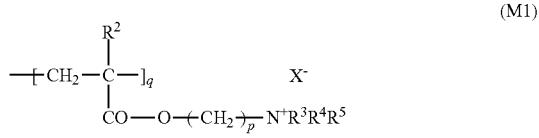

(M1)

wherein $R^2$ is or —$CH_3$; $R^3$, $R^4$ and $R^5$ are independently chosen from ($C_1$ to $C_4$) alkyl, ($C_1$ to $C_4$) alkenyl or ($C_2$ to $C_4$) hydroxyalkyl groups; p=1, 2, 3 or 4; q is a natural number; and $X^-$ is a physiologically compatible organic or inorganic anion, as well as copolymers, essentially consisting of monomer units listed in formula (M1) as well as non-ionic monomer units, are suitable cationic film-forming and/or cationic setting polymers. Regarding these polymers, those that are preferred in accordance with the invention meet at least one of the following conditions:

$R^2$ is a methyl group;
$R^3$, $R^4$ and $R^5$ are methyl groups; and
m has the value 2 or 3.

Exemplary physiologically compatible counter ions X— of Formula (M1) include halide ions, sulfate ions, phosphate ions, methosulfate ions as well as organic ions such as lactate, citrate, tartrate and acetate ions. Halide ions are preferred, particularly chloride.

A very suitable homopolymer is the optionally crosslinked poly(methacryloyloxyethyltrimethylammonium chloride) with the INCI name Polyquaternium-37. Such products are commercially available under the trade names Rheocare® CTH (Cosmetic Rheologies) and Synthalen® CR (Ethnichem). Crosslinking can be effected, when desired, with the help of olefinically polyunsaturated compounds, for example divinylbenzene, tetraallyloxyethane, methylene bisacrylamide, diallyl ether, polyallyl polyglyceryl ether, or allyl ethers of sugars or sugar derivatives such as erythritol, pentaerythritol, arabitol, mannitol, sorbitol, sucrose or glucose. Methylene bisacrylamide is a preferred crosslinking agent.

The homopolymer is preferably employed in the form of a non-aqueous polymer dispersion that should have a polymer content of not less than 30% by weight. Such polymer dispersions are commercially available under the names Salcare® SC 95 (ca. 50% polymer content, additional components: mineral oil (INCI name: Mineral Oil) and tridecyl-polyoxypropylene polyoxyethylene ether (INCI name: PPG-1-Trideceth-6)) and Salcare® SC 96 (ca. 50% polymer content, additional components: mixture of diesters of propylene glycol with a mixture of caprylic- and capric acid (INCI name: Propylene Glycol Dicaprylate/Dicaprate) and tridecyl-polyoxypropylene polyoxyethylene ether (INCI name: PPG-1-Trideceth-6)).

Copolymers of quaternized derivatives of dialkylaminoalkyl(meth)acrylate and/or copolymers of quaternized derivatives of dialkylaminoalkyl(meth)acrylamide are particularly preferred suitable cationic film-forming and/or cationic setting polymers.

Copolymers with monomer units according to formula (M1) preferably comprise acrylamide, methacrylamide, $C_{1-4}$ alkyl esters of acrylic acid and $C_{1-4}$ alkyl esters of methacrylic acid as the non-ionic monomer units. Acrylamide is particularly preferred among these non-ionic monomers. These copolymers can also be crosslinked, as in the case of the above described homopolymers. An inventively preferred copolymer is the crosslinked acrylamide/methacryloyloxyethyltrimethylammonium chloride copolymer. Such copolymers, in which the monomers are present in a weight ratio of about 20:80, are commercially available as a ca. 50% conc. non-aqueous polymer dispersion named Salcare® SC 92.

A further inventively preferred suitable cationic film-forming and/or cationic setting polymer is at least one cationic polymer that comprises at least one structural element of Formula (M9) and additionally at least one structural element of Formula (M10)—

(M9)

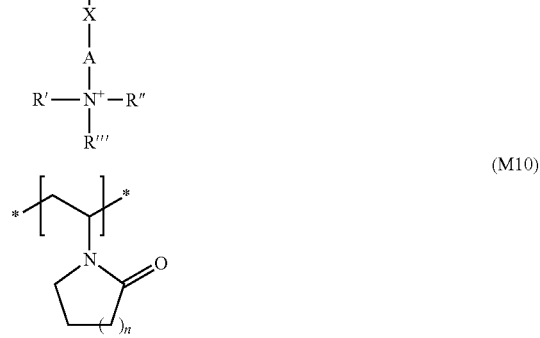

(M10)

wherein
R is hydrogen or a methyl group,
R', R" and R'" are independently a ($C_1$ to $C_{30}$) alkyl group,
X is oxygen or an NH group,
A us an ethane-1,2-diyl group or a propane-1,3-diyl group, and
n is 1 or 3.

To compensate for the positive polymer charge, all possible physiologically acceptable anions may be used, such as chloride, bromide, hydrogen sulfate, methyl sulfate, ethyl sulfate, tetrafluoroborate, phosphate, hydrogen phosphate, dihydrogen phosphate or p-toluene sulfonate, triflate.

Exemplary compounds of this type include copolymers of dimethylaminoethyl methacrylate, quaternized with diethyl sulfate, with vinyl pyrrolidone having the INCI name Polyquaternium-11 under the trade names Gafquat® 440, Gafquat® 734, Gafquat® 755 (each from ISP) and Luviquat PQ 11 PN (BASF SE).

Furthermore, cationic polymers are inventively particularly preferably chosen from cationic, quaternized cellulose derivatives.

Moreover, cationic, quaternized cellulose derivatives are preferred suitable film-forming and/or setting polymers.

Those cationic, quaternized celluloses that carry more than one permanent cationic charge in a side chain have proven to be particularly advantageous in the context of the invention. Among these cationic celluloses, once again those cationic celluloses with the INCI name Polyquaternium-4 are particularly suitable, which, for example, are marketed by the National Starch company under the trade names Celquat® H 100, Celquat® L 200.

In the context of the invention, copolymers having at least one structural element of Formula (M11) additionally serve as quite particularly preferred usable cationic polymers—

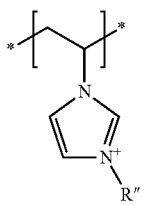 (M11)

wherein
R″ is a (C$_1$ to C$_4$) alkyl group, particularly a methyl group, and additionally possesses at least one further cationic and/or non-ionic structural element.

To compensate for the positive polymer charge, all possible physiologically acceptable anions may be used, such as chloride, bromide, hydrogen sulfate, methyl sulfate, ethyl sulfate, tetrafluoroborate, phosphate, hydrogen phosphate, dihydrogen phosphate or p-toluene sulfonate, triflate.

It is again inventively preferred when at least one copolymer (c1) that, in addition to at least one structural element of Formula (M11), further contains a structural element of Formula (M6), is comprised as the additional cationic polymer—

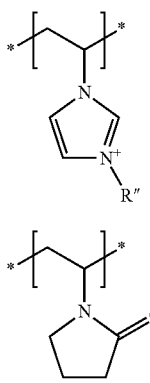

(M11)

(M6)

wherein
R″ is a (C$_1$ to C$_4$) alkyl group, particularly a methyl group.

To compensate for the positive polymer charge of copolymer (cl), all possible physiologically acceptable anions may be used, such as chloride, bromide, hydrogen sulfate, methyl sulfate, ethyl sulfate, tetrafluoroborate, phosphate, hydrogen phosphate, dihydrogen phosphate or p-toluene sulfonate, triflate.

Cationic film-forming and/or cationic setting polymers that are quite particularly preferred as the copolymers (c1) comprise 10 to 30 mol %, preferably 15 to 25 mol % and particularly 20 mol % of structural units according to Formula (M11), and 70 to 90 mol %, preferably 75 to 85 mol % and particularly 80 mol % of structural units according to Formula (M6).

In this regard it is particularly preferred when copolymers (c1) comprise, in addition to polymer units resulting from the incorporation of the cited structural units according to Formula (M11) and (M6) into the copolymer, a maximum 5 wt. %, preferably a maximum 1 wt. % of polymer units that trace back to the incorporation of other monomers. Copolymers (c1) are preferably exclusively constituted from structural units of Formula (M11) where R″=methyl and (M6), and can be described by the general Formula (Poly1)—

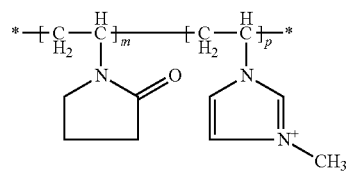 (Poly1)

wherein m and p vary according to the molecular mass of the polymer and are not intended to mean to portray block copolymers. In fact, structural units of Formula (M11) and Formula (M6) can be statistically distributed in the molecule.

If a chloride ion is used to compensate the positive charge of the polymer of Formula (Poly1), then these N-methyl vinyl imidazole/vinyl pyrrolidone copolymers are named according to INCI nomenclature as Polyquaternium-16 and are available from for example BASF under the trade names Luviquat® Style, Luviquat® FC 370, Luviquat® FC 550, Luviquat® FC 905 and Luviquat® HM 552.

If a methosulfate ion is used to compensate the positive charge of the polymer of Formula (Poly1), then these N-methyl vinylimidazole/vinyl pyrrolidone copolymers are named according to INCI nomenclature as Polyquaternium-44 and are available from for example BASF under the trade name Luviquat® UltraCare.

Particularly preferred inventive agents comprise a copolymer (c1), especially of Formula (Poly1), which has molecular masses within a defined range. Here, inventive agents are preferred, in which the molecular mass of the copolymer (c1) is from 50 to 400 kDa, preferably from 100 to 300 kDa, more preferably from 150 to 250 kDa and particularly from 190 to 210 kDa.

In addition to the copolymer(s) (c1) or instead of it or them, the inventive agents can also comprise copolymers (c2) that starting from the copolymer (c1) possess as the additional structural units structural units of Formula (M7)—

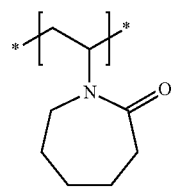 (M7)

Further particularly preferred agents according to the invention are accordingly those that comprise as the cationic film-forming and/or cationic setting polymer at least one copolymer (c2) having at least one structural unit according to Formula (M11-a) and at least one structural unit according to Formula (M6) and at least one structural unit according to Formula (M7)—

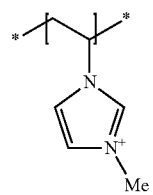 (M11-a)

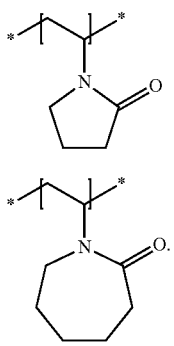
(M6)

(M7)

Also in this regard it is particularly preferred when the copolymers (c2) comprise, in addition to polymer units that result from the incorporation of the cited structural units in accordance with Formula (M11-a), (M6) and (M7) into the copolymer, maximum 5 wt. %, preferably maximum 1 wt. % of polymer units that trace back to the incorporation of other monomers. The copolymers (c2) are preferably exclusively constituted from structural units of Formula (M11-a), (M6) and (M7) and can be described by the general Formula (Poly2)—

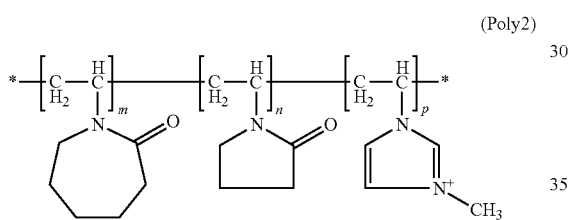
(Poly2)

wherein each of the indices m, n and p vary according to the molecular mass of the polymer and are not intended to mean to portray block copolymers. In fact, structural units of the cited Formulas can be statistically distributed in the molecule.

To compensate for the positive polymer charge of the component (c2), all possible physiologically acceptable anions may be used, such as for example chloride, bromide, hydrogen sulfate, methyl sulfate, ethyl sulfate, tetrafluoroborate, phosphate, hydrogen phosphate, dihydrogen phosphate or p-toluene sulfonate, triflate.

If a methosulfate ion is used to compensate the positive charge of the polymer of Formula (Poly2), then these N-methyl vinylimidazole/vinyl pyrrolidone/vinyl caprolactam copolymers are named according to INCI nomenclature as Polyquaternium-46 and are available from for example BASF under the trade name Luviquat® Hold.

Quite particularly preferred copolymers (c2) comprise 1 to 20 mol %, preferably 5 to 15 mol % and particularly 10 mol % of structural units in accordance with Formula (M11-a) and 30 to 50 mol %, preferably 35 to 45 mol % and particularly 40 mol % of structural units in accordance with Formula (M6) and 40 to 60 mol %, preferably 45 to 55 mol % and particularly 60 mol % of structural units in accordance with Formula (M7).

Particularly preferred inventive agents comprise a copolymer (c2) that has molecular masses within a defined range. Here, inventive agents are preferred, in which the molecular mass of the copolymer (c2) is from 100 to 1000 kDa, preferably from 250 to 900 kDa, more preferably from 500 to 850 kDa and particularly from 650 to 710 kDa.

In addition to the copolymer(s) (c1) and/or (c2) or in its or their place the agents according to the invention can also comprise copolymers (c3) as the film-forming cationic and/or setting cationic polymer which possess as the structural units structural units of the Formulas (M11-a) and (M6), as well as additional structural units from the group of the vinyl imidazole units and further structural units from the group of the acrylamide and/or methacrylamide units.

Quite particularly preferred agents according to the invention comprise as the additional cationic film-forming and/or cationic setting polymer at least one cationic polymer (hereinafter copolymer c3) that comprises at least one structural unit according to Formula (M11-a) and at least one structural unit according to Formula (M6) and at least one structural unit according to Formula (M10) and at least one structural unit according to Formula (M12)—

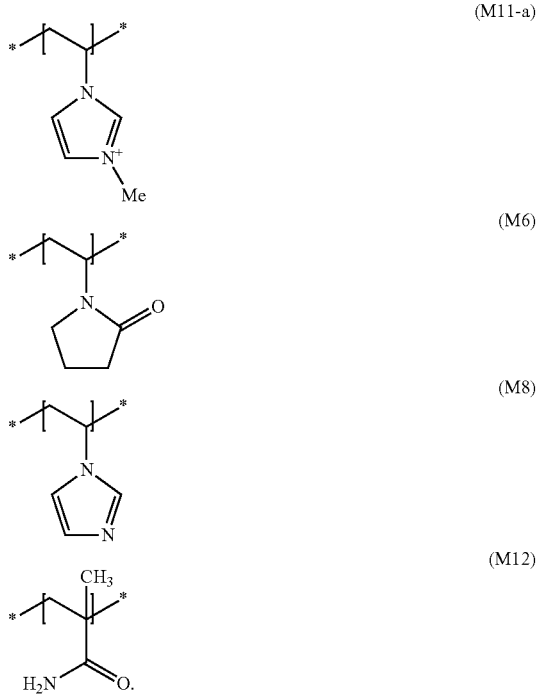

Also in this regard it is particularly preferred when copolymers (c3) comprise, in addition to polymer units that result from the incorporation of the cited structural units in accordance with Formula (M11-a), (M6), (M8) and (M12) into the copolymer, maximum 5 wt. %, preferably maximum 1 wt. % of polymer units that trace back to the incorporation of other monomers. The copolymers (c3) are preferably exclusively constituted from structural units of Formula (M11-a), (M6), (M8) and (M12) and can be described by the general Formula (Poly3)—

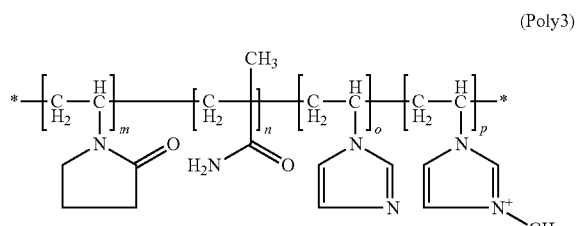
(Poly3)

wherein each of m, n, o and p vary according to the molecular mass of the polymer and are not intended to mean to portray block copolymers. In fact, structural units of Formula (M11-a), (M6), (M8) and (M12) can be statistically distributed in the molecule.

To compensate for the positive polymer charge of the component (c3), all possible physiologically acceptable anions may be used, such as for example chloride, bromide, hydrogen sulfate, methyl sulfate, ethyl sulfate, tetrafluoroborate, phosphate, hydrogen phosphate, dihydrogen phosphate or p-toluene sulfonate, triflate.

If a methosulfate ion is used to compensate the positive charge of the polymer of Formula (Poly3), then these N-methyl vinyl imidazole/vinyl pyrrolidone/vinyl imidazole/methacrylamide copolymers are named according to INCI nomenclature as Polyquaternium-68 and are available from for example BASF under the trade name Luviquat® Supreme.

Quite particularly preferred copolymers (c3) comprise 1 to 12 mol %, preferably 3 to 9 mol % and particularly 6 mol % of structural units in accordance with Formula (M11-a) and 45 to 65 mol %, preferably 50 to 60 mol % and particularly 55 mol % of structural units in accordance with Formula (M6) and 1 to 20 mol %, preferably 5 to 15 mol % and particularly 10 mol % of structural units in accordance with Formula (M8) and 20 to 40 mol %, preferably 25 to 35 mol % and particularly 29 mol % of structural units in accordance with Formula (M12).

Particularly preferred inventive agents comprise a copolymer (c3) that has molecular masses within a defined range. Here, inventive agents are preferred, in which the molecular mass of the copolymer (c3) is from 100 to 500 kDa, preferably from 150 to 400 kDa, more preferably from 250 to 350 kDa and particularly from 290 to 310 kDa.

The film-forming and/or setting polymer is quite particularly preferably selected from an N-vinyl pyrrolidone/methacrylamide/N-vinyl imidazole/1-vinyl-3-methyl-1H-imidazolium quaterpolymer.

Preferred additional film-forming cationic and/or setting polymers chosen from cationic polymers with at least one structural element of the above Formula (M11-a) include—
  vinyl pyrrolidone/1-vinyl-3-methyl-1H-imidazolium chloride copolymers (such as that with the INCI name Polyquaternium-16, sold under the trade names Luviquat® Style, Luviquat® FC 370, Luviquat® FC 550, Luviquat® FC 905 and Luviquat® HM 552 (BASF SE)),
  vinyl pyrrolidone/1-vinyl-3-methyl-1H-imidazolium methyl sulfate copolymers (such as that with the INCI name Polyquaternium-44 sold under the trade name Luviquat® Care (BASF SE)),
  vinyl pyrrolidone/vinyl caprolactam/1-vinyl-3-methyl-1H-imidazolium terpolymer (such as that with the INCI name Polyquaternium-46 sold under the trade names Luviquat® Care or Luviquat® Hold (BASF SE)),
  vinyl pyrrolidone/methacrylamide/vinyl imidazole/1-vinyl-3-methyl-1H-imidazolium methyl sulfate copolymer (such as that with the INCI name Polyquaternium-68 sold under the trade name Luviquat® Supreme (BASF SE)),
as well as mixtures of these polymers. The last-named polymer is quite particularly preferred.

The following embodiments (J) to (R) illustrate quite particularly preferred embodiments of the agent according to the invention.

(J): An agent for treating keratin-containing fibers, especially human hair, comprising in a cosmetically acceptable carrier—
  (a) at least one crosslinked, amphiphilic, anionic polymer, containing at least one structural unit of Formula (I) and at least one structural unit of Formula (II-a)—

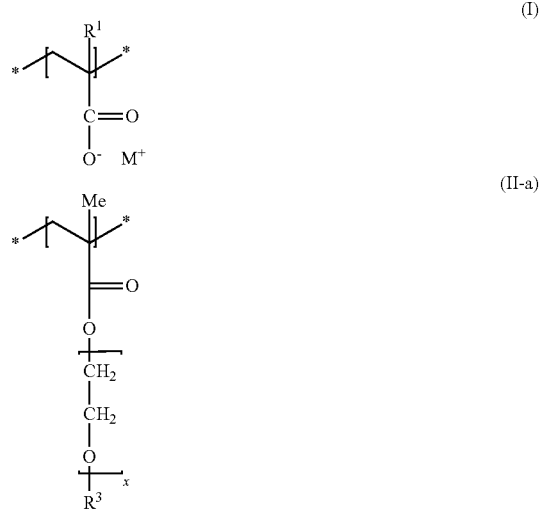

wherein
$R^1$ is a hydrogen atom or a methyl group,
$R^3$ is a ($C_8$ to $C_{30}$) alkyl group,
$M^+$ is a physiologically acceptable cation, and
x is a whole number from 5 to 35, especially a whole number from 10 to 24; and
  (b) at least one uncrosslinked amphiphilic, anionic polymer, containing at least one structural unit of Formula (III) and at least one structural unit of Formula (IV)

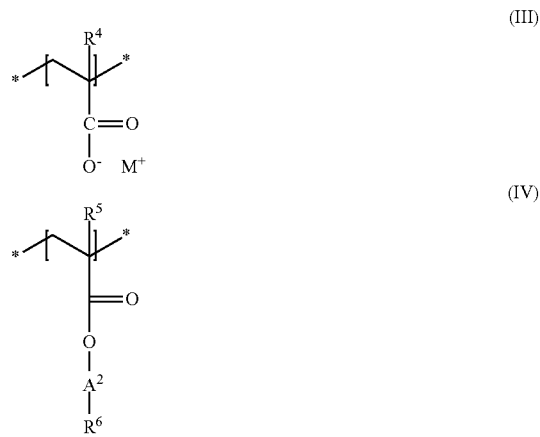

wherein
$R^4$ and $R^5$ are independently a hydrogen atom or a methyl group,
$R^6$ is a ($C_8$ to $C_{30}$) alkyl group,
$M^+$ is a physiologically acceptable cation, and
$A^2$ is *—$(CH_2CH_2O)_x$—* wherein x is a whole number from 5 to 35, *—$(CH_2CHMeO)_y$—* wherein y is a whole number from 5 to 35, or *—$(CH_2CH_2O)_x$—$(CH_2CHMeO)_y$—* wherein the sum of x+y is a whole number from 5 to 35 and x and y are greater than zero; and
  (c) at least one cationic copolymer containing at least one structural unit of Formula (M11-a) and at least one structural unit of Formula (M6) and at least one structural unit of Formula (M10) and at least one structural unit of Formula (M12)

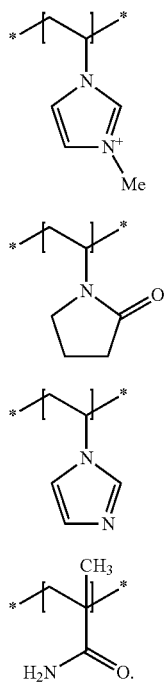

(M11-a)

(M6)

(M8)

(M12)

(K): An agent for treating keratin-containing fibers, especially human hair, comprising in a cosmetically acceptable carrier—

(a) at least one crosslinked, amphiphilic, anionic polymer, containing at least one structural unit of Formula (I) and at least one structural unit of Formula (II)—

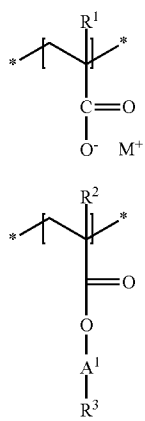

(I)

(II)

wherein
$R^1$ and $R^2$ are independently a hydrogen atom or a methyl group,
$R^3$ is a ($C_8$ to $C_{30}$) alkyl group,
$M^+$ is a physiologically acceptable cation, and
$A^1$ is *—$(CH_2CH_2O)_x$—* wherein x is a whole number from 5 to 35, *—$(CH_2CHMeO)_y$—* wherein y is a whole number from 5 to 35, or *—$(CH_2CH_2O)_x$— $(CH_2CHMeO)_y$—* wherein the sum x+y is a whole number from 5 to 35 and x and y are greater than zero;

(b) at least one uncrosslinked amphiphilic, anionic polymer, containing at least one structural unit of Formula (III) and at least one structural unit of Formula (IV-a)

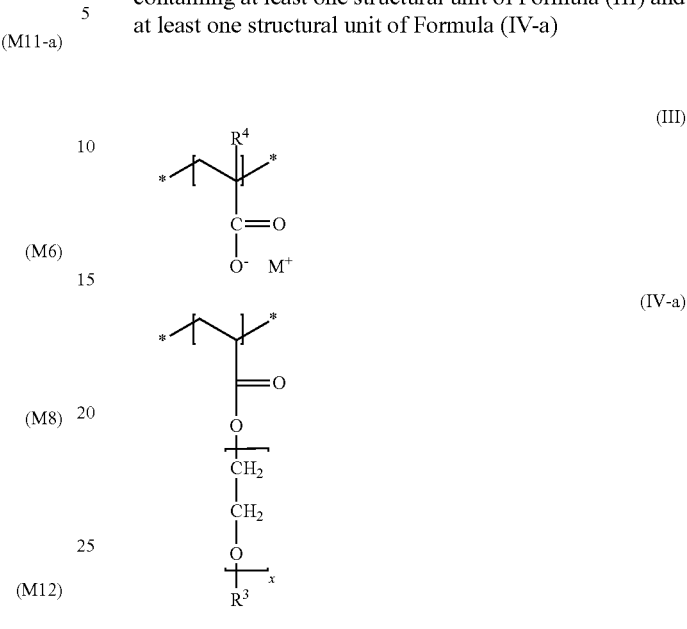

(III)

(IV-a)

wherein
$R^4$ is a hydrogen atom or a methyl group,
$R^3$ is a ($C_8$ to $C_{30}$) alkyl group,
$M^+$ is a physiologically acceptable cation, and
x is a whole number from 5 to 35, especially a whole number from 15 to 30; and (c) at least one cationic copolymer containing at least one structural unit of Formula (M11-a) and at least one structural unit of Formula (M6) and at least one structural unit of Formula (M10) and at least one structural unit of Formula (M12)

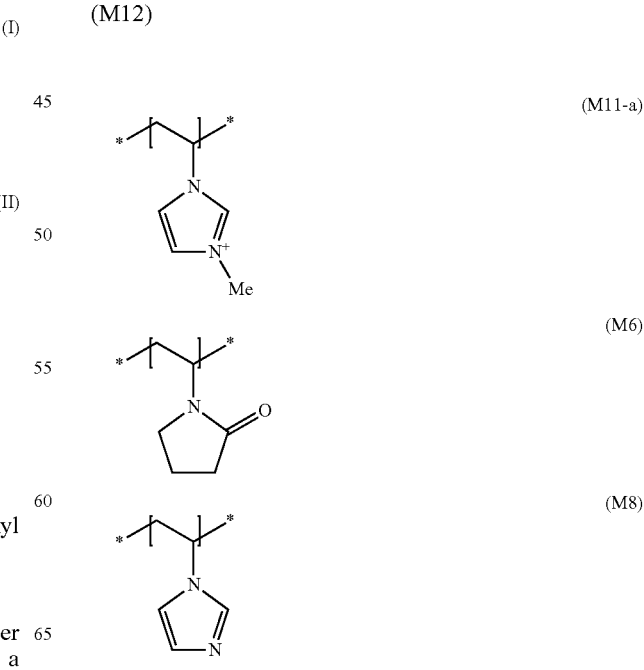

(M11-a)

(M6)

(M8)

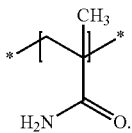

(L): An agent for treating keratin-containing fibers, especially human hair, comprising in a cosmetically acceptable carrier—
(a) at least one crosslinked, amphiphilic, anionic polymer, containing at least one structural unit of Formula (I) and at least one structural unit of Formula (II-a)—

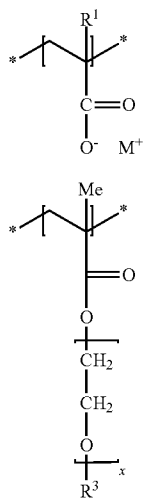

wherein
R$^1$ is a hydrogen atom or a methyl group,
R$^3$ is a (C$_8$ to C$_{30}$) alkyl group,
M$^+$ is a physiologically acceptable cation, and
x is a whole number from 5 to 35, especially a whole number from 10 to 24;
(b) at least one uncrosslinked amphiphilic, anionic polymer, containing at least one structural unit of Formula (III) and at least one structural unit of Formula (IV-a)

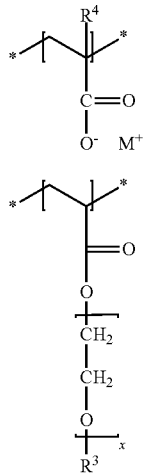

wherein
R$^4$ is a hydrogen atom or a methyl group,
R$^3$ is a (C$_8$ to C$_{30}$) alkyl group,
M$^+$ is a physiologically acceptable cation, and
x is a whole number from 5 to 35, especially a whole number from 15 to 30; and
(c) at least one cationic copolymer containing at least one structural unit of Formula (M11-a) and at least one structural unit of Formula (M6) and at least one structural unit of Formula (M10) and at least one structural unit of Formula (M12)

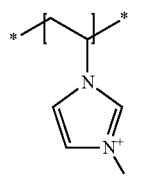

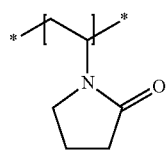

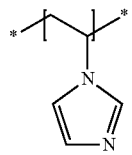

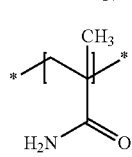

(M): An agent for treating keratin-containing fibers, especially human hair, comprising in a cosmetically acceptable carrier—
(a) 0.1 wt. % to 5.0 wt. %, preferably 0.2 wt. % to 2 wt. %, more preferably 0.2 wt. % to 1.5 wt. %, based on total weight of the agent, of at least one crosslinked, amphiphilic, anionic polymer containing at least one structural unit of Formula (I) and at least one structural unit of Formula (II-a)—

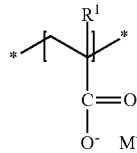

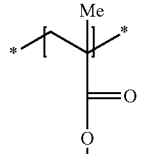

wherein
R$^1$ is a hydrogen atom or a methyl group,
R$^3$ is a (C$_8$ to C$_{30}$) alkyl group, $M^+$ is a physiologically acceptable cation, and x is a whole number from 5 to 35, especially a whole number from 10 to 24;

(b) 0.1 wt. % to 5.0 wt. %, preferably 0.2 wt. % to 5.0 wt. %, more preferably 0.1 wt. % to 2.0 wt. %, based on total weight of the agent, of at least one uncrosslinked amphiphilic, anionic polymer containing at least one structural unit of Formula (III) and at least one structural unit of Formula (IV)

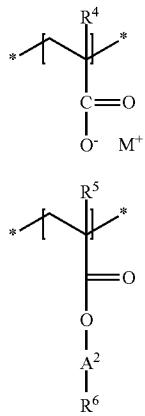

(III)

(IV)

wherein $R^4$ and $R^5$ are independently a hydrogen atom or a methyl group, $R^6$ is a ($C_8$ to $C_{30}$) alkyl group, $M^+$ is a physiologically acceptable cation, and $A^2$ is *—$(CH_2CH_2O)_x$—* wherein x is a whole number from 5 to 35, *—$(CH_2CHMeO)_y$—* wherein y is a whole number from 5 to 35, or *—$(CH_2CH_2O)_x$—$(CH_2CHMeO)_y$—* wherein the sum of x+y is a whole number from 5 to 35 and x and y are greater than zero; and (c) 0.01 wt. % to 10.0 wt. %, preferably 0.5 wt. % to 8.0 wt. %, more preferably 0.5 wt. % to 5.0 wt. %, based on total weight of the agent, of at least one cationic copolymer containing at least one structural unit of Formula (M11-a) and at least one structural unit of Formula (M6) and at least one structural unit of Formula (M10) and at least one structural unit of Formula (M12)

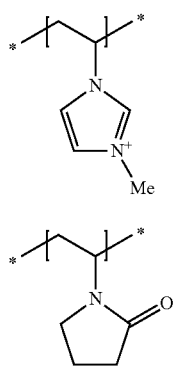

(M11-a)

(M6)

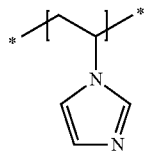

(M8)

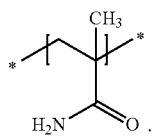

(M12)

(N): An agent for treating keratin-containing fibers, especially human hair, comprising in a cosmetically acceptable carrier—

(a) 0.1 wt. % to 5.0 wt. %, preferably 0.2 wt. % to 2 wt. %, more preferably 0.2 wt. % to 1.5 wt. %, based on total weight of the agent, of at least one crosslinked, amphiphilic, anionic polymer containing at least one structural unit of Formula (I) and at least one structural unit of Formula (II)—

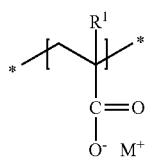

(I)

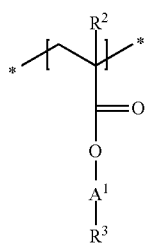

(II)

wherein $R^1$ and $R^2$ are independently a hydrogen atom or a methyl group, $R^3$ is a ($C_8$ to $C_{30}$) alkyl group, $M^+$ is a physiologically acceptable cation, and $A^1$ is *—$(CH_2CH_2O)_x$—* wherein x is a whole number from 5 to 35, *—$(CH_2CHMeO)_y$—* wherein y is a whole number from 5 to 35, or *—$(CH_2CH_2O)_x$—$(CH_2CHMeO)_y$—* wherein the sum x+y is a whole number from 5 to 35 and x and y are greater than zero; and (b) 0.1 wt. % to 5.0 wt. %, preferably 0.2 wt. % to 5.0 wt. %, more preferably 0.1 wt. % to 2.0 wt. %, based on total weight of the agent, of at least one uncrosslinked amphiphilic, anionic polymer containing at least one structural unit of Formula (III) and at least one structural unit of Formula (IV-a)

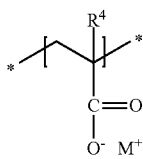
(III)

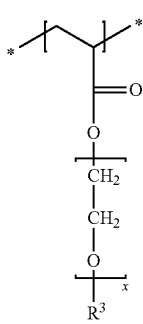
(IV-a)

wherein
$R^4$ is a hydrogen atom or a methyl group,
$R^3$ is a ($C_8$ to $C_{30}$) alkyl group,
$M^+$ is a physiologically acceptable cation, and
x is a whole number from 5 to 35, especially a whole number from 15 to 30; and (c) 0.01 wt. % to 10.0 wt. %, preferably 0.5 wt. % to 8.0 wt. %, more preferably 0.5 wt. % to 5.0 wt. %, based on total weight of the agent, of at least one cationic copolymer containing at least one structural unit of Formula (M11-a) and at least one structural unit of Formula (M6) and at least one structural unit of Formula (M10) and at least one structural unit of Formula (M12)

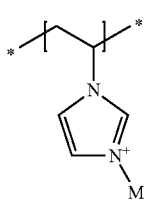
(M11-a)

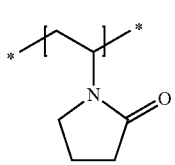
(M6)

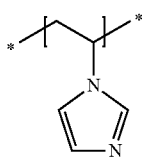
(M8)

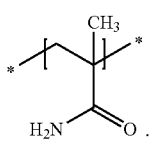
(M12)

(O): An agent for treating keratin-containing fibers, especially human hair, comprising in a cosmetically acceptable carrier—

(a) 0.1 wt. % to 5.0 wt. %, preferably 0.2 wt. % to 2 wt. %, more preferably 0.2 wt. % to 1.5 wt. %, based on total weight of the agent, of at least one crosslinked, amphiphilic, anionic polymer containing at least one structural unit of Formula (I) and at least one structural unit of Formula (II-a)—

(I)

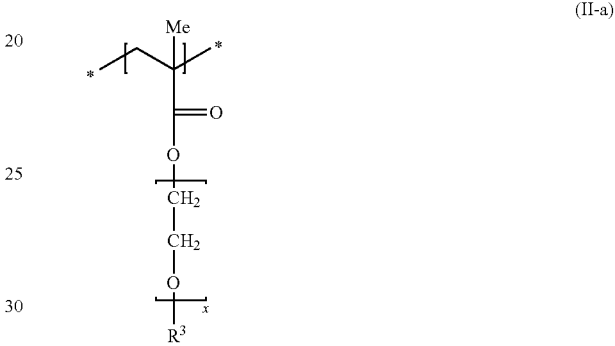
(II-a)

wherein
$R^1$ is a hydrogen atom or a methyl group,
$R^3$ is a ($C_8$ to $C_{30}$) alkyl group,
$M^+$ is a physiologically acceptable cation, and
x is a whole number from 5 to 35, especially a whole number from 10 to 24;

(b) 0.1 wt. % to 5.0 wt. %, preferably 0.2 wt. % to 5.0 wt. %, more preferably 0.1 wt. % to 2.0 wt. %, based on total weight of the agent, of at least one uncrosslinked amphiphilic, anionic polymer containing at least one structural unit of Formula (III) and at least one structural unit of Formula (IV-a)

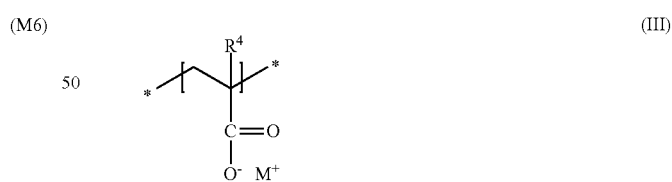
(III)

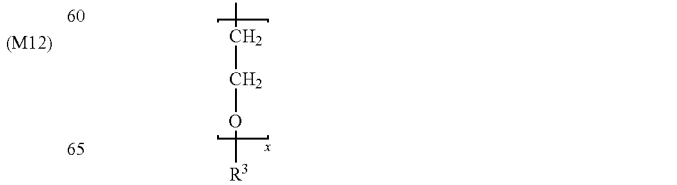
(IV-a)

wherein

R⁴ is a hydrogen atom or a methyl group,

R³ is a ($C_8$ to $C_{30}$) alkyl group,

M⁺ is a physiologically acceptable cation, and x is a whole number from 5 to 35, especially a whole number from 15 to 30; and (c) 0.01 wt. % to 10.0 wt. %, preferably 0.5 wt. % to 8.0 wt. %, more preferably 0.5 wt. % to 5.0 wt. %, based on total weight of the agent, of at least one cationic copolymer containing at least one structural unit of Formula (M11-a) and at least one structural unit of Formula (M6) and at least one structural unit of Formula (M10) and at least one structural unit of Formula (M12)

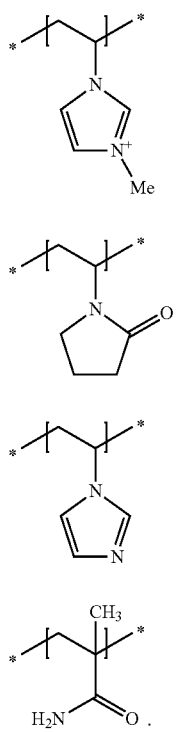

(M11-a)

(M6)

(M8)

(M12)

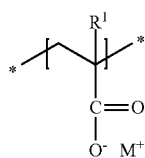

(P): An agent for treating keratin-containing fibers, especially human hair, comprising in a cosmetically acceptable carrier—

(a) 0.1 wt. % to 5.0 wt. %, preferably 0.2 wt. % to 2 wt. %, more preferably 0.2 wt. % to 1.5 wt. %, based on total weight of the agent, of at least one crosslinked, amphiphilic, anionic polymer containing at least one structural unit of Formula (I) and at least one structural unit of Formula (II-a)—

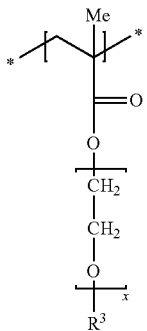

(I)

(II-a)

wherein

R¹ is a hydrogen atom or a methyl group,

R³ is a ($C_8$ to $C_{30}$) alkyl group,

M⁺ is a physiologically acceptable cation, and x is a whole number from 5 to 35, especially a whole number from 10 to 24;

(b) 0.1 wt. % to 5.0 wt. %, preferably 0.2 wt. % to 5.0 wt. %, more preferably 0.1 wt. % to 2.0 wt. %, based on total weight of the agent, of at least one uncrosslinked amphiphilic, anionic polymer containing at least one structural unit of Formula (III) and at least one structural unit of Formula (IV)

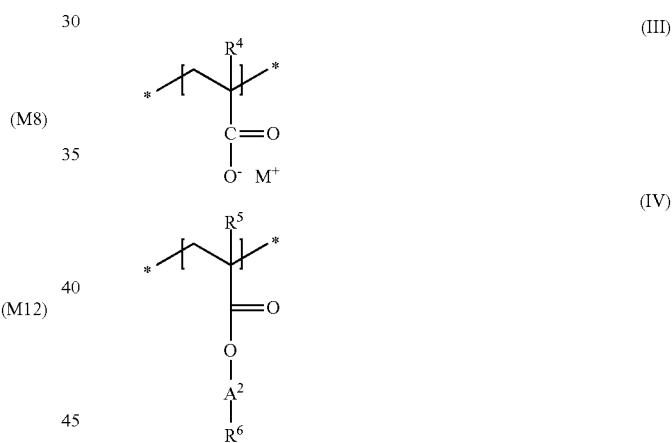

(III)

(IV)

wherein

R⁴ and R⁵ are independently a hydrogen atom or a methyl group,

R⁶ is a ($C_g$ to $C_{30}$) alkyl group,

M⁺ is a physiologically acceptable cation, and

A² is *—(CH₂CH₂O)$_x$—* wherein x is a whole number from 5 to 35, *—(CH₂CHMeO)$_y$—* wherein y is a whole number from 5 to 35, or, *—(CH₂CH₂O)$_x$—(CH₂CHMeO)$_y$—* wherein the sum of x+y is a whole number from 5 to 35 and x and y are greater than zero;

in a weight ratio [polymer (a) to polymer (b)] of 1 to 5 to 5 to 1, preferably 1 to 2 to 5 to 1, and more preferably 1 to 1.5 to 2 to 1; and (c) 0.01 wt. % to 10.0 wt. %, preferably 0.5 wt. % to 8.0 wt. %, more preferably 0.5 wt. % to 5.0 wt. %, based on total weight of the agent, of at least one cationic copolymer containing at least one structural unit of Formula (M11-a) and at least one structural unit of Formula (M6) and at least one structural unit of Formula (M10) and at least one structural unit of Formula (M12)

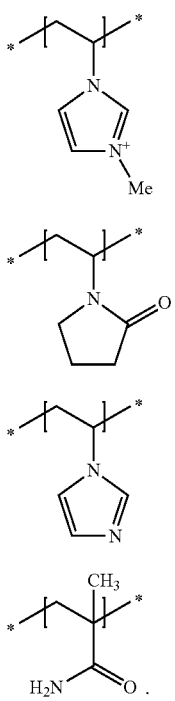

(M11-a)

(M6)

(M8)

(M12)

(Q): An agent for treating keratin-containing fibers, especially human hair, comprising in a cosmetically acceptable carrier—

(a) 0.1 wt. % to 5.0 wt. %, preferably 0.2 wt. % to 2 wt. %, more preferably 0.2 wt. % to 1.5 wt. %, based on total weight of the agent, of at least one crosslinked, amphiphilic, anionic polymer containing at least one structural unit of Formula (I) and at least one structural unit of Formula (II)—

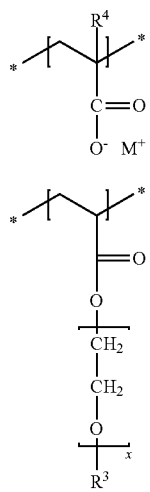

(I)

(II)

wherein $R^1$ and $R^2$ are independently a hydrogen atom or a methyl group, $R^3$ is a ($C_8$ to $C_{30}$) alkyl group, $M^+$ is a physiologically acceptable cation, and $A^1$ is *—$(CH_2CH_2O)_x$—* wherein x is a whole number from 5 to 35, *—$(CH_2CHMeO)_y$—* wherein y is a whole number from 5 to 35, or *—$(CH_2CH_2O)_x$—$(CH_2CHMeO)_y$—* wherein the sum x+y is a whole number from 5 to 35 and x and y are greater than zero; and (b) 0.1 wt. % to 5.0 wt. %, preferably 0.2 wt. % to 5.0 wt. %, more preferably 0.1 wt. % to 2.0 wt. %, based on total weight of the agent, of at least one uncrosslinked amphiphilic, anionic polymer containing at least one structural unit of Formula (III) and at least one structural unit of Formula (IV-a)

(III)

(IV-a)

wherein $R^4$ is a hydrogen atom or a methyl group, $R^3$ is a ($C_8$ to $C_{30}$) alkyl group, $M^+$ is a physiologically acceptable cation, and x is a whole number from 5 to 35, especially a whole number from 15 to 30;

in a weight ratio [polymer (a) to polymer (b)] of 1 to 5 to 5 to 1, preferably 1 to 2 to 5 to 1, and more preferably 1 to 1.5 to 2 to 1; and (c) 0.01 wt. % to 10.0 wt. %, preferably 0.5 wt. % to 8.0 wt. %, more preferably 0.5 wt. % to 5.0 wt. %, based on total weight of the agent, of at least one cationic copolymer containing at least one structural unit of Formula (M11-a) and at least one structural unit of Formula (M6) and at least one structural unit of Formula (M10) and at least one structural unit of Formula (M12)

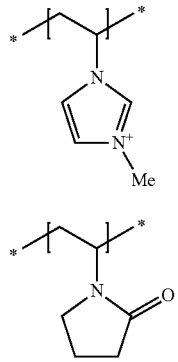

(M11-a)

(M6)

-continued

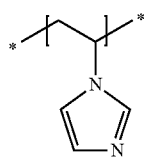
(M8)

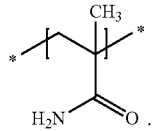
(M12)

(R): An agent for treating keratin-containing fibers, especially human hair, comprising in a cosmetically acceptable carrier—

(a) 0.1 wt. % to 5.0 wt. %, preferably 0.2 wt. % to 2 wt. %, more preferably 0.2 wt. % to 1.5 wt. %, based on total weight of the agent, of at least one crosslinked, amphiphilic, anionic polymer containing at least one structural unit of Formula (I) and at least one structural unit of Formula (II-a)—

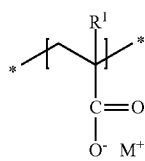
(I)

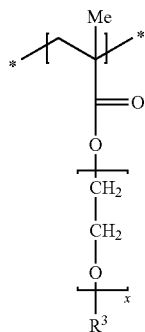
(II-a)

wherein $R^1$ is a hydrogen atom or a methyl group, $R^3$ is a ($C_8$ to $C_{30}$) alkyl group, $M^+$ is a physiologically acceptable cation, and x is a whole number from 5 to 35, especially a whole number from 10 to 24;

(b) 0.1 wt. % to 5.0 wt. %, preferably 0.2 wt. % to 5.0 wt. %, more preferably 0.1 wt. % to 2.0 wt. %, based on total weight of the agent, of at least one uncrosslinked amphiphilic, anionic polymer containing at least one structural unit of Formula (III) and at least one structural unit of Formula (IV-a)

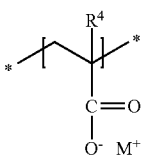
(III)

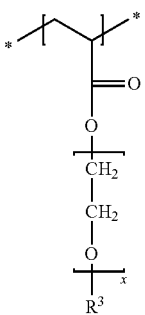
(IV-a)

wherein $R^4$ is a hydrogen atom or a methyl group, $R^3$ is a ($C_8$ to $C_{30}$) alkyl group, $M^+$ is a physiologically acceptable cation, and x is a whole number from 5 to 35, especially a whole number from 15 to 30;

in a weight ratio [polymer (a) to polymer (b)] of 1 to 5 to 5 to 1, preferably 1 to 2 to 5 to 1, and more preferably 1 to 1.5 to 2 to 1; and (c) 0.01 wt. % to 10.0 wt. %, preferably 0.5 wt. % to 8.0 wt. %, more preferably 0.5 wt. % to 5.0 wt. %, based on total weight of the agent, of at least one cationic copolymer containing at least one structural unit of Formula (M11-a) and at least one structural unit of Formula (M6) and at least one structural unit of Formula (M10) and at least one structural unit of Formula (M12)

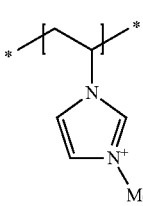
(M11-a)

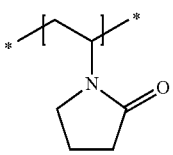
(M6)

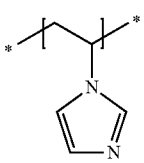
(M8)

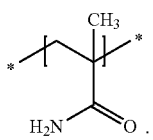 (M12)

Further preferred cationic polymers that can be employed in the inventive agents are the "temporarily cationic" polymers. These polymers usually comprise an amino group that is present at specific pH values as a quaternary ammonium group and is thus cationic.

These polymers include, for example, chitosan. In the context of the present invention, chitosan and/or chitosan derivatives are considered as quite particularly preferred suitable film-forming and/or setting polymers.

Chitosans are biopolymers and are considered to be in the group of hydrocolloids. From a chemical point of view, they are partially deacetylated chitins of different molecular weight.

Chitosan is manufactured from chitin, preferably from the remains of crustacean shells, which are available in large quantities as a cheap raw material. For this, the chitin is firstly deproteinated by adding bases, demineralized by adding mineral acids and finally deacetylated by adding strong bases, wherein the molecular weights can vary over a wide spectrum. Those types are preferably employed that have an average molecular weight of 800 000 to 1 200 000 Dalton, a viscosity according to Brookfield (1 wt. % conc. in glycolic acid) below 5000 mPas, a deacetylation degree in the range 80 to 88% and an ash content of less than 0.3 wt. %.

In the scope of the invention, in addition to chitosans as typical cationic biopolymers, cationically derivatized chitosans can also be considered (e.g., quaternized products) or alkoxylated chitosans.

Inventively preferred agents comprise neutralization products of chitosan neutralized with at least one acid, chosen from lactic acid, pyrrolidone carboxylic acid, nicotinic acid, hydroxy-iso-butyric acid, hydroxy-iso-valeric acid, or contain mixtures of these neutralization products as the chitosan derivative(s).

Exemplary suitable chitosan (derivatives) are freely available on the market under the trade names Hydagen® CMF (1 wt. % active substance in aqueous solution with 0.4 wt. % glycolic acid, molecular weight 500,000 to 5,000,000 g/mol Cognis), Hydagen® HCMF (chitosan (80% deacetylated), molecular weight 50,000 to 1,000,000 g/mol, Cognis), Kytamer® PC (80 wt. % active substance of chitosan pyrrolidone carboxylate (INCI name: Chitosan PCA), Amerchol) and Chitolam® NB/101.

Agents according to the invention preferably comprise chitosan or its derivatives in an amount of 0.01 wt. % to 20.0 wt. %, more preferably 0.01 wt. % to 10.0 wt. %, quite particularly preferably 0.1 wt. % to 1 wt. %, based on total weight of the agent according to the invention.

In the context of the invention, preferred suitable temporarily cationic polymers also include those having at least one structural unit of Formulae (M1-1) to (M1-8)—

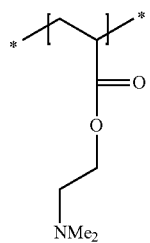 (M1-1)

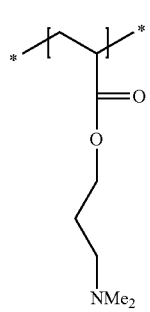 (M1-2)

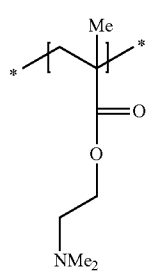 (M1-3)

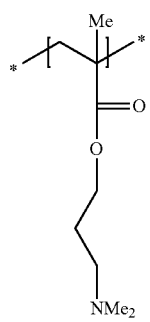 (M1-4)

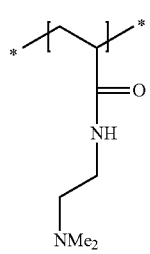 (M1-5)

-continued

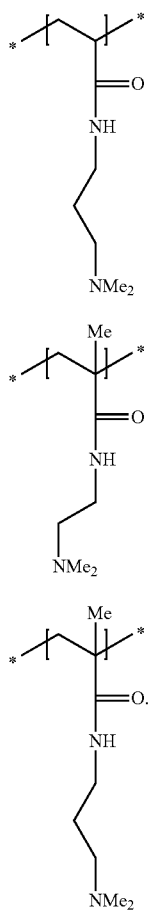
(M1-6)

(M1-7)

(M1-8)

In this regard, those copolymers are again preferred that have at least one structural unit of Formulae (M1-1) to (M1-8) as well as at least one structural unit of Formula (M10)—

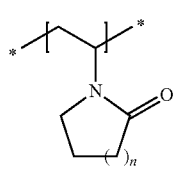
(M10)

wherein n is 1 or 3.

Here again the following group of polymers—
vinyl caprolactam/vinyl pyrrolidone/dimethylaminoethyl methacrylate copolymer (for example INCI name: Vinyl Caprolactam/PVP/Di-methylaminoethyl Methacrylate Copolymer under the trade name Gaffix® VC 713 (ISP)),
vinyl pyrrolidone/vinyl caprolactam/dimethylaminopropylmethacrylamide copolymer (for example INCI name: VP/Vinyl Caprolactam/DMAPA Acrylates Copolymer under the trade name Aquaflex® SF-40 (ISP)),
vinyl caprolactam/vinyl pyrrolidone/dimethylaminoethyl methacrylate copolymer (for example as a 35-39% solids in ethanol in the form of the commercial product Advantage LC E with the INCI name: Vinyl Caprolactam/VP/Dimethylaminoethyl Methacrylate Copolymer, Alcohol, Lauryl Pyrrolidone (ISP)),
vinyl pyrrolidone/dimethylaminopropylmethacrylamide copolymer (for example INCI name: VP/DMAPA Acrylates Copolymer under the trade name Styleze® CC-10 (ISP)),
form the preferred list for selection.

Agents according to the invention can also have at least one amphoteric polymer as the film-forming and/or setting polymer. Amphoteric polymers include not only those polymers whose molecule have both free amino groups and free —COOH or SO$_3$H groups and which are capable of forming inner salts, but also zwitterionic polymers whose molecule comprises quaternary ammonium groups and —COO$^-$ or —SO$_3^-$ groups, and those polymers comprising —COOH or SO$_3$H groups and quaternary ammonium groups.

An example of an amphopolymer which may be used in accordance with the invention is the acrylic resin obtainable under the designation Amphomer®, which is a copolymer of tert-butylaminoethyl methacrylate, N-(1,1,3,3-tetramethylbutyl)acrylamide, and two or more monomers from the group consisting of acrylic acid, methacrylic acid and their simple esters.

The latter, in addition to the cationogenic group or positively charged group, have at least one negatively charged group in the molecule, and are also called zwitterionic polymers. Preferred employable zwitterionic polymers are essentially composed of
A) Monomers with quaternary ammonium groups of the general Formula (Z-I)—

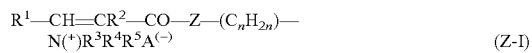

$$R^1\!\!-\!\!CH\!\!=\!\!CR^2\!\!-\!\!CO\!\!-\!\!Z\!\!-\!\!(C_nH_{2n})\!\!-\!\!N(^+)R^3R^4R^5 A^{(-)} \quad (Z\text{-}I)$$

wherein $R^1$ and $R^2$ are independently hydrogen or a methyl group; $R^3$, $R^4$ and $R^5$ are independently alkyl groups having 1 to 4 carbon atoms; Z is an NH-group or an oxygen atom; n is a whole number from 2 to 5; and $A^{(-)}$ is the anion of an organic or inorganic acid; and
B) monomers of carboxylic acids of general Formula (Z-II)—

$$R^6\!\!-\!\!CH\!\!=\!\!CR^7\!\!-\!\!COOH \quad (Z\text{-}II)$$

wherein $R^6$ and $R^7$ are independently hydrogen or methyl groups.

According to the invention, these compounds can be added directly as well as in salt form, the latter being obtained, for example, by neutralization of the polymer with an alkali hydroxide. Quite particularly preferred are such polymers which incorporate monomers of type (Z-I), wherein $R^3$, $R^4$ and $R^5$ are methyl groups, Z is an NH group and $A^{(-)}$ is a halide, methoxysulfate or ethoxysulfate ion. Acrylamidopropyltrimethylammonium chloride is a particularly preferred monomer (Z-II). Acrylic acid is preferably used as the monomer (Z-II) in the cited polymers.

Suitable starting monomers include dimethylaminoethyl acrylamide, dimethylaminoethyl methacrylamide, dimethylaminopropyl acrylamide, dimethylaminopropyl methacrylamide and diethylaminoethyl acrylamide, if Z means an NH group or dimethylaminoethyl acrylate, dimethylaminoethyl methacrylate and diethylaminoethyl acrylate, if Z is an oxygen atom.

The monomers comprising a tertiary amino group are then quaternized in the usual manner, wherein methyl chloride, dimethyl sulfate or diethyl sulfate are particularly suitable as the alkylation reagents. The quaternization reaction can be made in aqueous solution or in a solvent.

Advantageously, those monomers of formula (Z-I) are used which are derivatives of acrylamide or methacrylamide.

In addition, those monomers having halide, methoxysulfate or ethoxysulfate ions as the counter ions are preferred. Those monomers of formula (Z-I) wherein $R^3$, $R^4$ and $R^5$ are methyl groups, are likewise preferred.

Acrylamidopropyltrimethylammonium chloride is a quite particularly preferred monomer of formula (Z-I).

Acrylic acid, methacrylic acid, crotonic acid and 2-methylcrotonic acid are suitable as monomeric carboxylic acids of formula (Z-II). Acrylic acid or methacrylic acid, particularly acrylic acid, is preferably employed.

Agents according to the invention preferably comprise amphoteric polymers in quantities of 0.01 to 20 wt. %, particularly preferably 0.05 to 10 wt. %, based on total agent. Quantities of 0.1 to 5.0% by weight are quite particularly preferred.

Furthermore, at least one anionic film-forming and/or anionic setting polymer can be employed as the film-forming and/or setting polymers.

Anionic polymers concern anionic polymers having carboxylate and/or sulfonate groups. Exemplary anionic monomers from which such polymers can be made are acrylic acid, methacrylic acid, crotonic acid, maleic anhydride and 2-acrylamido-2-methylpropane sulfonic acid. Here, the acidic groups may be fully or partially present as sodium, potassium, ammonium, mono- or triethanolammonium salts.

Within this embodiment, it can be preferred to use copolymers of at least one anionic monomer and at least one non-ionic monomer. Regarding the anionic monomers, reference is made to the abovementioned substances. Preferred non-ionic monomers are acrylamide, methacrylamide, acrylic acid esters, methacrylic acid esters, vinyl pyrrolidone, vinyl ethers and vinyl esters.

Preferred anionic copolymers are acrylic acid-acrylamide copolymers and particularly polyacrylamide copolymers with monomers that contain sulfonic acid groups. A particularly preferred anionic copolymer consists of 70 to 55 mole % acrylamide and 30 to 45 mole % 2-acrylamido-2-methylpropane sulfonic acid, wherein the sulfonic acid group may be fully or partially present as the sodium, potassium, ammonium, mono- or triethanolammonium salt. This copolymer can also be crosslinked, wherein the preferred crosslinking agents include polyolefinically unsaturated compounds such as tetraallyloxyethane, allyl sucrose, allyl pentaerythritol and methylene bisacrylamide. Such a polymer is comprised in the commercial product Sepigel®305 from the SEPPIC company. The use of this compound, which comprises a mixture of hydrocarbons ($C_{13}$-$C_{14}$ isoparaffins) and a non-ionic emulsifier (Laureth-7) besides the polymer components, has proved to be particularly advantageous in the context of the inventive teaching.

The sodium acryloyl dimethyl taurate copolymers commercialized as a compound with isohexadecane and polysorbate 80, under the trade name Simulgel®600, have also proved to be particularly effective according to the invention.

Further preferred employable anionic polymers are chosen from:
- copolymers of vinyl acetate and crotonic acid (marketed, for example, as the commercial product Aristoflex® A 60 with the INCI name VA/Crotonates Copolymer by CIBA in a 60 wt. % conc. dispersion in isopropanol-water),
- copolymers of ethyl acrylate and methacrylic acid (marketed, for example, by BASF SE under the trade name Luviflex® Soft with an acid number of 84 to 105 under the INCI name Acrylates Copolymer in a ca. 20 to 30 wt. % conc. dispersion in water),
- Polyurethanes containing at least one carboxylic group (such as a copolymer of isophthalic acid, adipic acid, 1,6-hexane diol, neopentyl glycol and isophorone diisocyanate as marketed by BASF SE under the trade name Luviset® PUR with the INCI name Polyurethane-1).

When particularly strong acting thickening anionic polymers are used, then in a preferred embodiment care should be taken that the previously cited preferred viscosity criterion of the agent according to the invention is adhered to.

Copolymers of maleic anhydride and methyl vinyl ether, especially those with crosslinks are also color-conserving polymers. A maleic acid-methyl vinyl ether copolymer crosslinked with 1,9-decadiene is commercially available under the trade name Stabileze® QM.

In order to intensify the effect according to the invention, the agents preferably also comprise at least one surfactant, wherein in principal, non-ionic, anionic, cationic, ampholytic surfactants are suitable. The group of ampholytic or amphoteric surfactants includes zwitterionic surfactants and ampholytes. According to the invention, the surfactants can have an emulsifying action.

Agents according to the invention preferably comprise additional surfactants in an amount of 0.01 wt. % to 5.0 wt. %, particularly preferably 0.05 wt. % to 0.5 wt. %, based on total weight of the agent.

It has proved particularly preferable when agents according to the invention comprise at least one non-ionic surfactant.

Non-ionic surfactants comprise, for example, a polyol group, a polyalkylene glycol ether group or a combination of polyol ether groups and polyglycol ether groups as the hydrophilic group. Exemplary compounds of this type are—
- addition products of 2 to 100 moles ethylene oxide and/or 1 to 5 moles propylene oxide to linear and branched fatty alcohols containing 8 to 30 carbon atoms, to fatty acids containing 8 to 30 carbon atoms and to alkyl phenols containing 8 to 15 carbon atoms in the alkyl group,
- methyl or $C_2$-$C_6$ alkyl group end blocked addition products of 2 to 50 moles ethylene oxide and/or 1 to 5 moles propylene oxide to linear and branched fatty alcohols with 8 to 30 carbon atoms, to fatty acids with 8 to 30 carbon atoms and to alkyl phenols with 8 to 15 carbon atoms in the alkyl group, for example, the commercially available types Dehydrol® LS, Dehydrol® LT (Cognis),
- $C_{12}$-$C_{30}$ fatty acid mono- and diesters of addition products of 1 to 30 moles ethylene oxide to glycerin,
- addition products of 5 to 60 moles ethylene oxide on castor oil and hydrogenated castor oil,
- polyol esters of fatty acids, such as the commercial product Hydagen® HSP (Cognis) or Sovermol types (Cognis),
- alkoxylated triglycerides,
- alkoxylated fatty acid alkyl esters of the formula (E4-I)

$$R^1CO\text{---}(OCH_2CHR^2)_wOR^3 \qquad (E4\text{-}I)$$

wherein $R^1CO$ is a linear or branched, saturated and/or unsaturated acyl group containing 6 to 22 carbon atoms; $R^2$ is hydrogen or methyl; $R^3$ is linear or branched alkyl groups containing 1 to 4 carbon atoms; and w is a number from 1 to 20,
- amine oxides,
- mixed hydroxy ethers, such as described in DE-OS 1 973 8866,
- sorbitol esters of fatty acids and addition products of ethylene oxide to sorbitol esters of fatty acids such as polysorbates,
- sugar esters of fatty acids and addition products of ethylene oxide to sugar esters of fatty acids,
- addition products of ethylene oxide to fatty acid alkanolamides and fatty amines,
- sugar surfactants of the type alkyl and alkenyl oligoglycosides according to Formula (E4-II), $$R^4O\text{-}[G]_p \qquad (E4\text{-}II)$$

wherein R⁴ is an alkyl or alkenyl group containing 4 to 22 carbon atoms; G is a sugar group containing 5 or 6 carbon atoms; and p is a number from 1 to 10. They can be obtained according to the appropriate methods of preparative organic chemistry.

Alkyl and alkenyl oligoglycosides can derive from aldoses or ketoses containing 5 or 6 carbon atoms, preferably from glucose. Preferred alkyl and/or alkenyl oligoglycosides are accordingly alkyl and/or alkenyl oligoglucosides. The index value p in general Formula (E4-II) represents the degree of oligomerization (DP) (i.e., the distribution of mono and oligoglycosides) and is a number from 1 to 10. Whereas in a given compound, p must be a whole number and preferably assumes the values p=1 to 6, the value p for a specific alkyl oligoglycoside is an analytically determined calculated quantity that mostly represents a fractional number. Preferably, alkyl and/or alkenyl oligoglycosides are employed with an average degree of oligomerization p of 1.1 to 3.0. From the industrial point of view, such alkyl and/or alkenyl oligoglycosides are preferred with degrees of oligomerization less than 1.7 and in particular between 1.2 and 1.4. The alkyl or alkenyl group R⁴ can be derived from primary alcohols containing 4 to 11, preferably 8 to 10 carbon atoms. Typical examples are butanols, caproyl alcohol, caprylic alcohol, capric alcohol and undecyl alcohol as well as their industrial mixtures, such as for example those obtained by the hydrogenation of industrial fatty acid methyl esters or in the course of the hydrogenation of aldehydes from the Roelen Oxo-synthesis. Alkyl oligoglucosides with chain lengths $C_8$-$C_{10}$ (DP=1 to 3) are preferred, which result as the low boiling fraction in the separative distillation of industrial $C_8$-$C_{18}$ coco fatty alcohol and which can be contaminated with a fraction of less than 6 wt. % of $C_{1-2}$ alcohol, as well as alkyl oligoglucosides based on industrial $C_{9/11}$ oxo alcohols (DP=1 to 3). The alkenyl group $R^{15}$ can moreover also be derived from primary alcohols containing 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol as well as their industrial mixtures that can be obtained as described above. Alkyl oligoglucosides based on hydrogenated $C_{12/14}$ coco alcohol with a DP of 1 to 3 are preferred.

non-ionic surfactants based on silicone, particularly from Dimethicone copolyols that are preferably alkoxylated, especially polyethoxylated or polypropoxylated. Among the Dimethicone copolyols, polyoxyalkylene-modified dimethylpolysiloxanes of general Formulae (E4-V) or (E4-VI) are inventively particularly preferably employed as the non-ionic surfactant:

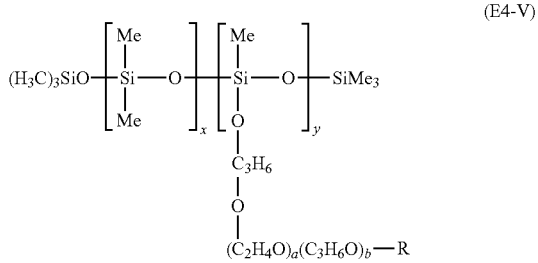

(E4-V)

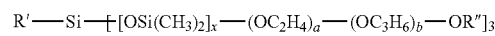

(E4-VI)

wherein

R is hydrogen, an alkyl group containing 1 to 12 carbon atoms, an alkoxy group containing 1 to 12 carbon atoms, or a hydroxyl group;

R' and R" are alkyl groups containing 1 to 12 carbon atoms;

x is a whole number from 1 to 100, preferably a whole number from 20 to 30;

y is a whole number from 1 to 20, preferably from 2 to 10; and a and b are whole numbers from 0 to 50, preferably from 10 to 30.

In the context of the invention, particularly preferred exemplary Dimethicone copolyols are the commercially marketed products named SILWET® (Union Carbide Corporation) and DOW CORNING (Dow).

Inventively particularly preferred Dimethicone copolyols are Dow Corning 190 and Dow Corning 193 Fluid (Dow Corning).

Alkylene oxide addition products to saturated, linear fatty alcohols and fatty acids, each with 2 to 100 moles ethylene oxide per mole fatty alcohol or fatty acid, have proved to be quite particularly preferred non-ionic surfactants. Similarly, preparations with excellent properties are obtained when they comprise $C_{12}$-$C_{30}$ fatty acid mono- and diesters of addition products of 1 to 30 moles ethylene oxide to glycerin and/or addition products of 5 to 60 moles ethylene oxide to castor oil and hydrogenated castor oil as the non-ionic surfactants.

Suitable anionic surfactants include all anionic surface-active materials suitable for use on the human body. They are characterized by a water solubilizing anionic group, such as a carboxylate, sulfate, sulfonate or phosphate group and a lipophilic alkyl group containing about 8 to 30 carbon atoms. In addition, the molecule may comprise glycol or polyglycol ether groups, ester, ether and amide groups as well as hydroxyl groups.

Agents according to the invention contain ingredients or active substances in a cosmetically acceptable carrier.

Preferred cosmetically acceptable carriers are aqueous, alcoholic or aqueous alcoholic media containing preferably at least 10 wt. % water, based on the total composition. In particular, lower alcohols containing 1 to 4 carbon atoms, such as for example ethanol and isopropanol, which are usually used for cosmetic purposes, can be comprised as alcohols.

Organic solvents or a mixture of solvents with a boiling point of less than 400° C. can be present as additional co-solvents in a quantity of 0.1 to 15 weight percent, preferably 1 to 10 weight percent, based on the total agent. Particularly suitable additional co-solvents are unbranched or branched hydrocarbons such as pentane, hexane, isopentane and cyclic hydrocarbons such as cyclopentane and cyclohexane. Additional, particularly preferred water-soluble solvents are glycerin, ethylene glycol and propylene glycol in an amount of up to 30 weight percent based on the total agent.

In particular, the addition of glycerin and/or propylene glycol and/or polyethylene glycol and/or polypropylene glycol increases the flexibility of the polymer film that is formed when the agent according to the invention is used. Consequently, if a more flexible hold is desired, then the agents according to the invention preferably comprise 0.01 to 30 wt.

% glycerin and/or propylene glycol and/or polyethylene glycol and/or polypropylene glycol, based on the total agent.

The agents preferably exhibit a pH of 2 to 11. The pH range is particularly preferably from 2 to 8. In the context of this publication, pH data refer to pH at 25° C. unless otherwise stated.

Agents according to the invention preferably further comprise at least one alkanolamine.

Inventively preferred are preferably chosen from primary amines containing a $C_2$-$C_6$ alkyl parent substance that carries at least one hydroxyl group. Particularly preferred alkanolamines are selected from the group consisting of 2-aminoethane-1-ol (monoethanolamine), 3-aminopropane-1-ol, 4-aminobutane-1-ol, 5-aminopentane-1-ol, 1-aminopropane-2-ol, 1-aminobutane-2-ol, 1-aminopentane-2-ol, 1-aminopentane-3-ol, 1-aminopentane-4-ol, 3-amino-2-methylpropane-1-ol, 1-amino-2-methylpropane-2-ol, 3-aminopropane-1,2-diol, 2-amino-2-methylpropane-1,3-diol. Inventively quite particularly preferred alkanolamines are selected from the group 2-aminoethane-1-ol, 2-amino-2-methylpropane-1-ol and 2-amino-2-methyl-propane-1,3-diol.

Agents according to the invention can additionally comprise auxiliaries and additives typically incorporated into styling agents.

In particular, care products may be mentioned as suitable auxiliaries and additives.

According to the invention, at least one silicone oil and/or at least one silicone gum is preferably employed as the care substance.

Suitable silicone oils or silicone gums according to the invention are especially dialkyl and alkylarylsiloxanes, such as, for example dimethylpolysiloxane and methylphenylpolysiloxane, as well as their alkoxylated, quaternized or also anionic derivatives. Cyclic and linear polydialkylsiloxanes, their alkoxylated and/or aminated derivatives, dihydroxypolydimethylsiloxanes and polyphenylalkylsiloxanes are preferred.

Silicone oils afford the most varied effects. Thus, for example, they simultaneously influence the dry and wet combability, the feel of the dry and wet hair as well as the gloss. The term, "silicone oils" is understood by the person skilled in the art to mean organosilicon compounds with a plurality of structures. In the first instance among these are understood the Dimethiconols (S1). They can be linear, branched, cyclic, or cyclic and branched. Linear Dimethiconols can be represented by the following structural formula (S1-I):

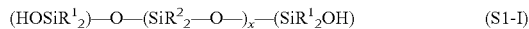

$$(HOSiR^1{}_2)-O-(SiR^2{}_2-O-)_x-(SiR^1{}_2OH) \qquad (S1-I)$$

Branched Dimethiconols can be represented by the following structural formula (S1-II):

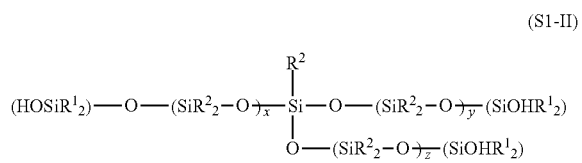

(S1-II)

wherein $R^1$ and $R^2$ are independently hydrogen, a methyl group, a $C_2$ to $C_{30}$ linear, saturated or unsaturated hydrocarbon group, a phenyl group and/or an aryl group. The following commercial products are examples of such products: Botanisil NU-150M (Botanigenics), Dow Corning 1-1254 Fluid, Dow Corning 2-9023 Fluid, Dow Corning 2-9026 Fluid, Ultrapure Dimethiconol (Ultra Chemical), Unisil SF-R (Universal Preserve), X-21-5619 (Shin-Etsu Chemical Co.), Abil OSW 5 (Degussa Care Specialties), ACC DL-9430 Emulsion (Taylor Chemical Company), AEC Dimethiconol & Sodium Dodecylbenzene sulfonate (A & E Connock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401 DC (all from Chemsil Silicones, Inc.), Dow Corning 1401 Fluid, Dow Corning 1403 Fluid, Dow Corning 1501 Fluid, Dow Corning 1784 HVF Emulsion, Dow Corning 9546 Silicone Elastomer Blend (all from Dow Corning Corporation), Dub Gel S11400 (Stearinerie Dubois Fils), HVM 4852 Emulsion (Crompton Corporation), Jeesilc 6056 (Jeen International Corporation), Lubrasil, Lubrasil DS (both from Guardian Laboratories), Nonychosine E, Nonychosine V (both from Exsymol), SanSurf Petrolatum-25, Satin Finish (both from Collaborative Laboratories, Inc.), Silatex-D30 (Cosmetic Ingredient Resources), Silsoft 148, Silsoft E-50, Silsoft E-623 (all from Crompton Corporation), SM555, SM2725, SM2765, SM2785 (all from GE Silicones), Taylor T-Sil CD-1, Taylor TME-4050E (all from Taylor Chemical Company), TH V 148 (Crompton Corporation), Tixogel CYD-1429 (Süd-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all from Wacker-Chemie GmbH).

Dimethicones (S2) form the second group of silicones that can be used according to the invention. They can be linear, branched, cyclic, or cyclic and branched. Linear Dimethicones can be represented by the following structural formula (S2-I)—

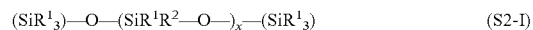

$$(SiR^1{}_3)-O-(SiR^1R^2-O-)_x-(SiR^1{}_3) \qquad (S2-I)$$

Branched Dimethicones can be represented by the structural formula (S2-II)—

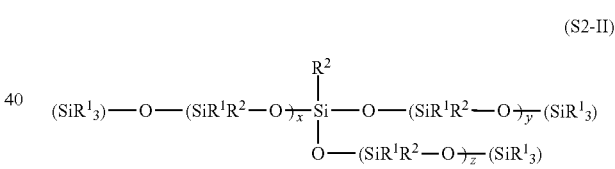

(S2-II)

$R^1$ and $R^2$ are independently hydrogen, a methyl group, a $C_2$ to $C_{30}$ linear, saturated or unsaturated hydrocarbon group, a phenyl group and/or an aryl group.

Dimethicone copolyols (S3) form a further group of suitable silicones. Dimethicone copolyols can be represented by the following structural formulae—

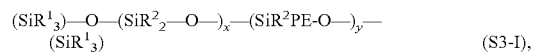

$$(SiR^1{}_3)-O-(SiR^2{}_2-O-)_x-(SiR^2PE-O-)_y- \\ (SiR^1{}_3) \qquad (S3-I),$$

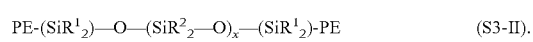

$$PE-(SiR^1{}_2)-O-(SiR^2{}_2-O)_x-(SiR^1{}_2)-PE \qquad (S3-II).$$

Branched Dimethicone copolyols can be represented by the following structural formula (S3-III)—

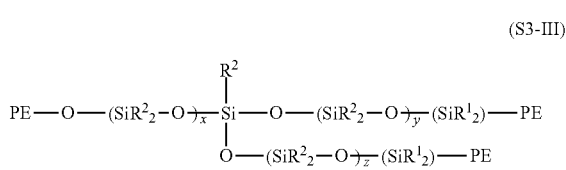

(S3-III)

or by the structural formula (S3-IV)—

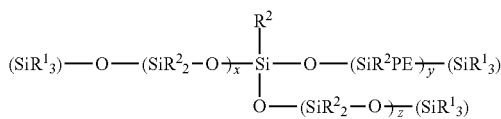
(S3-IV)

$R^1$ and $R^2$ are independently hydrogen, a methyl group, a $C_2$ to $C_{30}$ linear, saturated or unsaturated hydrocarbon group, a phenyl group and/or an aryl group. Suitable Dimethicone copolyols are commercially available and marketed, for example, by Dow Corning under the trade name Dow Corning® 5330 Fluid.

Naturally, Dimethiconols, Dimethicones and/or Dimethicone copolymers can already be present as an emulsion. The corresponding emulsions of Dimethiconols, Dimethicones and/or Dimethicone copolyols can be produced both after production of the corresponding Dimethiconols, Dimethicones and/or Dimethicone copolymols from these and usual emulsification processes known to one skilled in the art. Cationic, anionic, non-ionic or zwitterionic surfactants and emulsifiers can be used as auxiliaries and adjuvants for production of the corresponding emulsions. Naturally, emulsions of Dimethiconols, Dimethicones and/or Dimethicone copolyols can also be produced directly by an emulsion polymerization process. These types of processes are also well known to the person skilled in the art.

When Dimethiconols, Dimethicones and/or Dimethicone copolyols are used as an emulsion, then the droplet size of the emulsified particles ranges from 0.01 to 10,000 μm, preferably 0.01 to 100 μm, particularly preferably 0.01 to 20 μm and quite particularly preferably 0.01 to 10 μm. Particle size is determined by light scattering method.

If branched Dimethiconols, Dimethicones and/or Dimethicone copolyols are used, then it can be taken as understood that the branching is greater than a fortuitous branching that accidentally results from impurities in the respective monomers. Accordingly, in the context of the present invention, the degree of branching is understood to be greater than 0.01% for branched Dimethiconols, Dimethicones and/or Dimethicone copolyols. The degree of branching is preferably greater than 0.01% and quite particularly preferably greater than 0.5%. The degree of branching is determined from the ratio of the unbranched monomers to the branched monomers, i.e. the amount of tri- and tetrafunctional siloxanes. According to the invention, both low-branched as well as highly branched Dimethiconols, Dimethicones and/or Dimethicone copolyols can be quite particularly preferred.

Further suitable silicones are amino-functional silicones, especially the silicones compiled under the INCI name Amodimethicone. Consequently, it is inventively preferred when the agents according to the invention additionally comprise at least one amino-functional silicone. These are silicones having at least one, optionally substituted, amino group.

Such silicones can be described, for example, by Formula (S4-I)—

$$M(R_aQ_bSiO_{(4-a-b)/2})_x(R_cSiO_{(4-c)/2})_yM \quad (S4-I)$$

wherein R is a hydrocarbon or a hydrocarbon group with 1 to 6 carbon atoms; Q is a polar group of the general formula —$R^1Z$, wherein $R^1$ is a divalent, linking group that is bonded to hydrogen and the group Z, made up of carbon atoms and hydrogen atoms, carbon-, hydrogen- and oxygen atoms or carbon-, hydrogen- and nitrogen atoms, and Z is an organic amino functionalized group that comprises at least one amino functional group; "a" assumes values in the range of about 0 to about 2, "b" assumes values in the range of about 1 to about 3, "a"+"b" is less than or equal to 3; "c" is a number in the range of about 1 to about 3; x is a number in the range of 1 to about 2000, advantageously from about 3 to about 50 and most preferably from about 3 to about 25; y is a number in the range of about 20 to about 10,000, advantageously from about 125 to about 10,000 and most preferably from about 150 to about 1000; and M is a suitable silicone end-group, as is known from the prior art, preferably trimethylsiloxy. Z is an organic, amino functional group comprising at least one functional amino group. A possible formula for Z is $NH(CH_2)_zNH_2$, wherein z is a whole number from 1 to 50. Another possible formula for Z is —$NH(CH_2)_zNH(CH_2)_{zz}$, wherein z and zz are independently a whole number from 1 to 50, wherein this structure includes diamino ring structures such as piperazinyl. Particularly preferably, Z is a —$NHCH_2CH_2NH_2$ group. Another possible formula for Z is —$N(CH_2)_zNX^1X^2$ or —$NX^1X^2$, wherein $X^1$ and $X^2$ are independently chosen from hydrogen and an alkyl group containing 1 to about 6 carbon atoms. Q is quite particularly preferably a polar, amino functional group of the Formula

—$CH_2CH_2CH_2NHCH_2CH_2NH_2$.

The molar ratio of the $R_3Q_bSiO_{(4-a-b)/2}$ units to the $R_cSiO_{(4-c)/2}$ units is in the range from about 1:2 to 1:65, preferably from about 1:5 to about 1:65 and particularly preferably from about 1:15 to about 1:20. If one or a plurality of silicones of the above Formula is added, then the different variable substituents in the above Formula for the different silicone components present in the silicone mixture can be different.

Preferred amino functional silicones correspond to Formula (S4-II)—

$$R'_aG_{3-a}\text{-Si}(OSiG_2)_n\text{-}(OSiG_bR'_{2-b})_m\text{—}O\text{—SiG}_{3-a}\text{-}R'_a \quad (S4\text{-II}),$$

wherein:

G is —H, a phenyl group, —OH, —O—$CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$;

a is a number from 0 to 3, particularly 0;

b is a number from 0 to 1, particularly 1;

m and n are numbers whose sum (m+n) is from 1 to 2000, preferably from 50 to 150, wherein n preferably assumes values of 0 to 1999, particularly 49 to 149, and m preferably assumes values of 1 to 2000, particularly 1 to 10;

R' is a monovalent group chosen from

—$N(R'')$—$CH_2$—$CH_2$—$N(R'')_2$

—$N(R'')_2$

—$N^+(R'')_3 A^-$

—$N^+H(R'')_2 A^-$

—$N^+H_2(R'')A^-$

—$N(R'')$—$CH_2$—$CH_2$—$N^+R''H_2 A^-$, wherein each R'' is the same or different groups from the group —H, -phenyl, -benzyl, $C_1$-$C_{20}$ alkyl groups, preferably —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, and $A^-$ is an anion preferably chosen from chloride, bromide, iodide or methosulfate.

Particularly preferred amino functional silicones correspond to Formula (S4-III)—

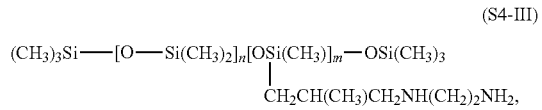 (S4-III)

wherein m and n are numbers whose sum (m+n) is from 1 to 2000, preferably from 50 to 150, wherein n preferably assumes values of 0 to 1999, particularly from 49 to 149, and m preferably assumes values of 1 to 2000, particularly 1 to 10.

These silicones are designated according to INCI nomenclature as Trimethylsilylamodimethicones.

Further amino functional silicones of Formula (S4-IV) are particularly preferred—

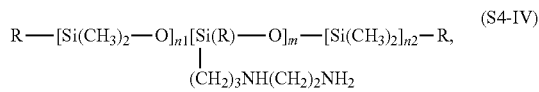 (S4-IV)

wherein R is —OH, —O—CH$_3$ or a —CH$_3$ group; and m, n1 and n2 are numbers whose sum (m+n1+n2) is from 1 to 2000, preferably from 50 to 150, wherein the sum (n1+n2) preferably assumes values of 0 to 1999, particularly from 49 to 149, and m preferably assumes values of 1 to 2000, particularly 1 to 10.

These silicones are designated as Amodimethicones according to the INCI nomenclature and are available, for example, in the form of an emulsion as the commercial product Dow Corning® 939 or as the commercial product Dow Corning® 949 in a mixture with a cationic and a non-ionic surfactant.

Preferably, those amino functional silicones are employed which have an amine number above 0.25 meq/g, preferably above 0.3 meq/g and particularly preferably above 0.4 meq/g. The amine number stands for milli-equivalents of amine per gram of amino functional silicone. It can be measured by titration and can also be reported with the unit mg KOH/g.

The agents preferably contain silicones in amounts of 0.01 wt. % to 15 wt. %, particularly preferably 0.05 to 2 wt. %, based on total agent.

The composition can comprise, for example, at least one protein hydrolyzate and/or one of its derivatives as a care substance of another compound class.

Protein hydrolyzates are product mixtures obtained by acid-, base- or enzyme-catalyzed degradation of proteins (albumins). According to the invention, the term "protein hydrolyzates" is also understood to mean total hydrolyzates as well as individual amino acids and their derivatives as well as mixtures of different amino acids. Furthermore, according to the invention, polymers built up from amino acids and amino acid derivatives are understood to be included in the term protein hydrolysates. The latter include polyalanine, polyasparagine, polyserine etc. Additional examples of usable compounds according to the invention are L-alanyl-L-proline, polyglycine, glycyl-L-glutamine or D/L-methionine-S-methyl sulfonium chloride. Of course, β-amino acids and their derivatives, like β-alanine, anthranilic acid or hippuric acid, can also be inventively added. The molecular weight of the protein hydrolyzates utilizable according to the invention ranges from 75, the molecular weight of glycine, to 200,000, preferably the molecular weight is 75 to 50,000 and quite particularly preferably 75 to 20,000 Dalton.

According to the invention, the added protein hydrolyzates can be vegetal as well as animal or marine or synthetic origin.

Animal protein hydrolysates include protein hydrolysates of elastin, collagen, keratin, silk and milk albumin, which can also be present in the form of their salts. Such products are marketed, for example, under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Sericin (Pentapharm) and Kerasol® (Croda).

Use of silk protein hydrolyzates is particularly interesting. Silk refers to fibers from the cocoon of the mulberry silk spinner (*Bombyx mori* L.). The raw silk fibers consist of a double stranded fibroin. Sericin is the intercellular cement that holds these double strands together. Silk consists of 70-80 wt. % fibroin, 19-28 wt. % sericin, 0.5-1 wt. % fat and 0.5-1 wt. % colorants and mineral constituents. The significant constituents of the sericin are ca. 46 wt. % hydroxy amino acids. The sericin consists of a group of 5 to 6 proteins. The significant amino acids of sericin are serine (Ser, 37 wt. %), aspartate (Asp, 26 wt. %), glycine (Gly, 17 wt. %), alanine (Ala), leucine (Leu) and tyrosine (Tyr).

The water-insoluble fibroin is one of the scleroproteins with a long chain molecular structure. The major constituents of fibroin are glycine (44 wt. %), alanine (26 wt. %), and tyrosine (13 wt. %). A further significant structural feature of fibroin is the hexapeptide sequence Ser-Gly-Ala-Gly-Ala-Gly.

Thus, for example, sericin is marketed by Pentapharm Ltd. as a commercial product with the name Sericin Code 303-02. Fibroin is offered far more frequently in the market as a protein hydrolyzate with different molecular weights. In particular, these hydrolyzates are marketed as "silk hydrolyzates". Thus, hydrolyzed fibroin with average molecular weights between 350 and 1000 is commercialised under the trade name Promois® Silk.

Protein hydrolyzates of vegetal origin (e.g., soya-, almond-, pea-, potato- and wheat protein hyrolyzates) are available, for example, under the trade names Gluadin® (Cognis), DiaMin® (Diamalt), Lexein® (Inolex), Hydrosoy® (Croda), Hydrolupin® (Croda), Hydrosesame® (Croda), Hydrotritium® (Croda) and Crotein® (Croda).

Although it is preferred to add the protein hydrolysates as such, optionally other mixtures containing amino acids can also be added in their place. Likewise, it is possible to add derivatives of protein hydrolysates, e.g. in the form of their fatty acid condensation products. Such products are marketed, for example, under the trade names Lamepon® (Cognis), Lexein® (Inolex), Crolastin® (Croda), Crosilk® (Croda) or Crotein® (Croda).

Naturally, the teaching according to the invention includes all isomeric forms, such as cis/trans isomers, diastereoisomers and chiral isomers.

According to the invention, it is also possible to employ a mixture of a plurality of protein hydrolyzates.

Agents according to the invention comprise protein hydrolyzates, for example, in concentrations of 0.01 wt. % to 20 wt. %, preferably 0.05 wt. % up to 15 wt. % and quite particularly preferably in amounts of 0.05 wt. % up to 5.0 wt. %, based on total weight of the end-use preparation.

Agents according to the invention can further comprise at least one vitamin, one provitamin, one vitamin precursor and/or one of their derivatives as the care substance.

According to the invention, such vitamins, provitamins and vitamin precursors are preferred which are normally classified in the groups A, B, C, E, F and H.

Retinol (vitamin $A_1$) as well as 3,4-didehydroretinol, (vitamin $A_2$) belong in the group of substances designated as vitamin A. β-carotene is the provitamin of retinol. Examples of suitable vitamin A components according to the invention are vitamin A acid and its esters, vitamin A aldehyde and vitamin A alcohol as well as its esters such as the palmitate and acetate. The agents preferably comprise the vitamin A components in amounts of 0.05 to 1 wt. %, based on the total end use preparation. The agents according to the invention preferably comprise vitamins, provitamins and vitamin precursors from groups A, B, C, E and H. Panthenol, pantolactone, pyridoxine and its derivatives as well as nicotinamide and biotin are especially preferred. D-panthenol is quite particularly preferably employed as the care substance.

Like the addition of glycerin and/or propylene glycol, the addition of panthenol increases the flexibility of the polymer film that is formed when the agent according to the invention is used. Thus, if a particularly flexible hold is desired, then the agents according to the invention can comprise panthenol instead of or in addition to glycerin and/or propylene glycol. In a preferred embodiment, the agents according to the invention comprise panthenol, preferably in a quantity of 0.05 to 10 wt. %, particularly preferably 0.1 to 5.0 wt. %, each based on the total agent.

Agents according to the invention can further comprise at least one plant extract as a care substance. Usually, these extracts are manufactured by extraction of the whole plant. In individual cases, however, it can also be preferred to produce the extracts solely from blossoms and/or leaves of the plant. With regard to the inventively usable plant extracts, reference is particularly made to extracts that are listed in the Table beginning on page 44 of the 3rd edition of the Guidelines for the Declaration of Ingredients in Cosmetics, (Leitfadens zur Inhaltsstoffdeklaration kosmetischer Mittel) published by the German Cosmetics, Toiletry, Perfumery and Detergent Association e.V. (IKW), Frankfurt. According to the invention, mainly extracts from green tea, oak bark, stinging nettle, hamamelis, hops, henna, camomile, burdock root, field horsetail, hawthorn, linden flowers, almonds, aloe vera, spruce needles, horse chestnut, sandal wood, juniper, coconut, mango, apricot, lime, wheat, kiwi, melon, orange, grapefruit, sage, rosemary, birch, malva, lady's smock, common yarrow, thyme, lemon balm, rest-harrow, coltsfoot, marshmallow (althaea), meristem, ginseng and ginger are preferred.

Mono- or oligosaccharides can also be incorporated as the care substance into the agents according to the invention.

Both monosaccharides as well as oligosaccharides such as raw sugar, lactose and raffinose can be incorporated. According to the invention, use of monosaccharides is preferred. Once again, monosaccharides preferably include those compounds having 5 or 6 carbon atoms.

Suitable pentoses and hexoses include ribose, arabinose, xylose, lyxose, allose, altrose, glucose, mannose, gulose, idose, galactose, talose, fucose and fructose. Arabinose, glucose, galactose and fructose are the preferred incorporated carbohydrates; glucose is quite particularly preferably incorporated, and is suitable both in the D(+) or L(−) configuration or as the racemate.

In addition, derivatives of these pentoses and hexoses can also be incorporated according to the invention, such as the corresponding onic and uronic acids (sugar acids), sugar alcohols, and glycosides.

Preferred sugar acids include gluconic acid, glucuronic acid, sugar acids, mannosugar acids and mucic acids. Preferred sugar alcohols are sorbitol, mannitol and dulcitol.

Preferred glycosides are methyl glucosides.

As the incorporated mono- and oligosaccharides are usually obtained from natural raw materials such as starch, they generally possess configurations that correspond to these raw materials (e.g., D-glucose, D-fructose and D-galactose).

The inventive agents preferably comprise mono- or oligosaccharides in an amount of 0.1 to 8 wt. %, particularly preferably 1 to 5 wt. %, based on total weight of the end-use preparation.

By addition of a UV filter, both the agent itself as well as the treated fibers can be protected against damage from UV radiation. Consequently, at least one UV filter is preferably added to the agent. The suitable UV filters are not generally limited in regard to their structure and their physical properties. Indeed, all UV filters that can be employed in the cosmetic field having an absorption maximum in the UVA (315-400 nm), in the UVB (280-315 nm) or in the UVC (<280 nm) regions are suitable. UV filters having an absorption maximum in the UVB region, especially in the range from about 280 to about 300 nm, are particularly preferred.

The inventively preferred UV-filters are chosen from substituted benzophenones, p-aminobenzoates, diphenylacrylates, cinnamates, salicylates, benzimidazoles and o-aminobenzoates. Moreover, it was found that for structurally similar UV filters, in many cases in the context of the inventive teaching, the water-insoluble compound exhibits a higher activity than that of water-soluble compounds that differ from them by one or a plurality of additional ionic groups. In the context of the invention, water-insoluble UV filters are understood to mean those that do not dissolve more than 1 wt. %, especially not more than 0.1 wt. % in water at 20° C. In addition, these compounds should be soluble to at least 0.1, especially to at least 1 wt. % in conventional cosmetic oil components at room temperature. Accordingly, the use of water-insoluble UV filters can be inventively preferred.

The agent usually contain UV filters in quantities of 0.01 to 1.0 wt. %, based on total weight of the end-use preparation.

In a particular embodiment, the agent further comprises one or more substantive dyes. Application of the agent then enables the treated keratinic fiber not only to be temporarily styled but also to be dyed at the same time. This can be particularly desirable when only a temporary dyeing is desired, for example with flamboyant fashion colors that can be subsequently removed from the keratinic fibers by simply washing them out.

Substantive dyes include nitrophenylenediamines, nitroamino phenols, azo dyes, anthraquinones or indophenols. Preferred substantive dyestuffs are the compounds with the international designations or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52 known compounds as well as 1,4-diamino-2-nitrobenzene, 2-amino-4-nitrophenol, 1,4-bis-(β-hydroxyethyl)-amino-2-nitrobenzene, 3-nitro-4-(β-hydroxyethyl)-amino phenol, 2-(2'-hydroxyethyl)amino-4,6-dinitrophenol, 1-(2'-hydroxyethyl)amino-4-methyl-2-nitrobenzene, 1-amino-4-(T-hydroxyethyl)-amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-1-hydroxy-4-nitrobenzene.

Cationic substantive dyes are preferably employed. Particular preference is given here to
(a) cationic triphenylmethane dyes, such as, for example, Basic Blue 7, Basic Blue 26, Basic Violet 2 and Basic Violet 14,
(b) aromatic systems which are substituted by a quaternary nitrogen group, such as Basic Yellow 57, Basic Red 76, Basic Blue 99, Basic Brown 16 and Basic Brown 17, and
(c) substantive dyes having a heterocycle that possesses at least one quaternary nitrogen atom. The compounds Basic Yellow 87, Basic Orange 31 and Basic Red 51 are quite particularly preferred cationic substantive dyes of group (c).

Cationic substantive dyes commercialized under the trade name Arianor® are likewise quite particularly preferred cationic substantive dyes according to the invention.

Inventive agents according to this embodiment include substantive dyes preferably in a quantity of 0.001 to 20 wt. %, based on total agent.

In addition, compositions according to the invention can also comprise naturally occurring dyestuffs as found, for example, in henna red, henna neutral, henna black, camomile leaves, sandalwood, black tea, alder buckthorn bark, sage, logwood, madder root, cachou, cedar and alkanet root.

It is not required that each substantive dyestuff be pure compounds. In fact, compositions according to the invention, due to manufacturing processes for the individual dyestuffs, may comprise minor quantities of even more components as long as these components have no detrimental affect on styling result or must be excluded on other grounds (e.g., toxicological).

Preferably, agents according to the invention are exempt from oxidation dye precursors. Oxidation dye precursors are divided into developer components and coupler components. Under the influence of oxidizing agents or from atmospheric oxygen, developer components form the actual colorants among each other or by coupling with one or more coupler components.

In addition to the cited components, compositions can furthermore comprise all active substances, additives and auxiliaries known for such preparations. Further exemplary active products, auxiliaries and additives include—
perfume oils;
solvents and solubilizers such as ethanol, isopropanol, ethylene glycol, propylene glycol, glycerin and diethylene glycol;
quaternized amines such as methyl-1-alkylamidoethyl-2-alkylimidazolinium methosulfate;
defoamers such as silicones;
anti-dandruff active materials such as Piroctone Olamine, zinc Omadine and Climbazole;
complexants such as EDTA, NTA, β-alanine diacetic acid and phosphonic acids;
swelling and penetration compositions such as glycerin, propylene glycol monoethyl ether, carbonates, hydrogen carbonates, guanidines, ureas, and primary, secondary and tertiary phosphates;
opacifiers such as latex, styrene/PVP copolymers and styrene/acrylamide copolymers;
pearlizing compositions such as ethylene glycol mono- and distearate as well as PEG-3 distearate;
preservatives; and
antioxidants.

Regarding these further optional ingredients and their amounts used, reference is expressly made to relevant handbooks known to one skilled in the art.

Formulation of inventive agents can be in all usual forms for styling agents, for example, in the form of solutions that can be applied as hair water or pump or aerosol spray onto the hair, in the form of creams, emulsions, waxes, gels or also surfactant-containing foaming solutions or other preparations suitable for application on the hair.

In the context of another embodiment, the agent is preferably in the form of a cream or a gel, particularly as a gel. Viscosity of agents in the form of creams or gels is preferably from 10,000 to 500,000 mPas, particularly preferably from 30,000 to 300,000 mPas (each measured with Brookfield RVDV II+ with Heilpath, Spindel T-E, 5 rpm, 20° C.).

If the agent is in the form of a gel, then it is particularly preferably a transparent gel.

A second subject matter of the invention is use of agents according to the invention for the temporary shaping of hair and/or for hair care.

Agents according to the invention and products that comprise these agents, especially hair gels or hair creams, lend to the treated hair a very strong, long-lasting hold to the hairstyle, although the hair remains flexible. If the agent is presented as a hair gel, then the gel has a pasty consistency that nevertheless can be uniformly dispersed on the hair without any dripping.

It is inventively preferred to use the agent of the first subject matter of the invention as a leave-on hair treatment agent.

A third subject matter of the invention is a method for treating keratin-containing fibers, especially human hair, in which method an inventive agent of the first subject matter is applied onto the keratin-containing fibers.

It is inventively preferred when the keratin-containing fibers are styled before, during or after the application of the agent according to the invention.

Furthermore, it is inventively preferred in the method according to the invention not to rinse out the agent from the keratin-containing fibers.

The following examples are intended to illustrate the subject matter of the present invention in more detail, without limiting it in any way.

EXAMPLES

Unless otherwise stated, the quantities are understood to be in weight percent.

The following composition was produced.

| Raw material | Wt. % |
| --- | --- |
| Triethanolamine | 0.79 |
| Amphomer® [1] | 0.80 |
| Luviquat Supreme® [2] | 4.50 |
| D-Panthenol | 0.15 |
| Euxyl® K 320 [3] | 0.80 |
| Synthalen® W 2000 [4] | 1.70 |
| Aculyn® 88 [5] | 2.00 |
| PEG hydrogenated castor oil | 0.20 |
| Uvinul® P 25 [6] | 0.10 |
| Perfume | 0.10 |
| Water | ad 100 |

[1] INCI name: Octylacrylamide/Acrylates/Butylaminoethyl Methacrylate Copolymer (National Starch);
[2] vinyl pyrrolidone-methacrylamide-vinyl imidazole-vinyl imidazolium methosulfate copolymer (55:29:10:6) (19-21% solids in water; INCI name: Polyquaternium-68) (BASF SE);
[3] mixture of phenoxyethanol, methylparaben, ethylparaben and propylene glycol (Schülke & Mayr);
[4] INCI name: Acrylates/Palmeth-25 Acrylate Copolymer (30-32 wt. % polymer in water) (3 V Sigma);
[5] copolymer of (meth)acrylic acid, (meth)acrylic acid esters and Steareth-20-methacrylic acid ester (28-30 wt. % solids in water; INCI name: Acrylates/Steareth-20 Methacrylate Crosspolymer) (Rohm und Haas);
[6] 1,4-ethoxylated (25 EO) ethyl aminobenzoate (INCI name: PEG25 PABA) (BASF).

The resulting product was storage-stable.

Excellent shape stabilization was achieved on application onto human hair.

We claim:

1. Agent for treating keratin-containing fibers, comprising in a cosmetically acceptable carrier:
   (a) acrylate/beheneth 25-methacrylate cross polymer present in an amount of 0.1 wt. % to 5.0 wt. %, based on total weight of the agent and
   b) acrylate/palmeth-25-acrylate copolymer present in an amount of 0.1 wt. % to 5.0 wt. %, based on total weight of the agent.

2. Agent according to claim 1 further comprising a film-forming and/or setting polymer.

3. Agent according to claim 2, wherein the film-forming and/or setting polymer is chosen from at least one cationic polymer having at least one structural unit according to Formula (M11-a) and at least one structural unit according to Formula (M6) and at least one structural unit according to Formula (M8) and at least one structural unit according to Formula (M12)

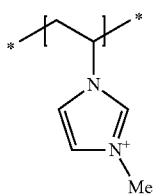

(M11-a)

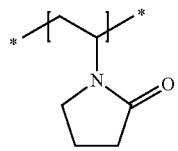

(M6)

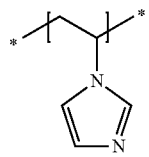

(M8)

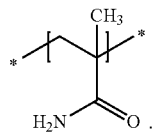

(M12)

4. Agent according to claim 2, wherein the film-forming and/or setting polymer is present in an amount of 0.01 wt. % to 20 wt. %, based on total weight of the agent.

5. Agent according to claim 1 further comprising at least one alkanolamine.

6. Method for treating keratin-containing fibers comprising applying an agent according to claim 1 onto the keratin-containing fibers.

* * * * *